(12) United States Patent
Fojtik et al.

(10) Patent No.: US 12,370,350 B2
(45) Date of Patent: *Jul. 29, 2025

(54) EXOSKELETON DEVICE WITH EXPANDABLE SECTION FOR SCORING

(71) Applicant: Transit Scientific, LLC, Salt Lake City, UT (US)

(72) Inventors: Shawn P. Fojtik, Park City, UT (US); Greg Method, Park City, UT (US); Jennifer Arnold, Salt Lake City, UT (US)

(73) Assignee: Transit Scientific, LLC, Salt Lake City, UT (US)

( * ) Notice: Subject to any disclaimer, the term of this patent is extended or adjusted under 35 U.S.C. 154(b) by 303 days.

This patent is subject to a terminal disclaimer.

(21) Appl. No.: 17/884,508

(22) Filed: Aug. 9, 2022

(65) Prior Publication Data

US 2022/0379099 A1 Dec. 1, 2022

Related U.S. Application Data

(63) Continuation of application No. 16/540,046, filed on Aug. 13, 2019, now Pat. No. 11,406,801, which is a continuation-in-part of application No. 16/174,205, filed on Oct. 29, 2018, now Pat. No. 11,179,549.

(60) Provisional application No. 62/623,117, filed on Jan. 29, 2018, provisional application No. 62/578,378, filed on Oct. 27, 2017.

(51) Int. Cl.
*A61M 25/10* (2013.01)

(52) U.S. Cl.
CPC ..... *A61M 25/104* (2013.01); *A61M 2025/105* (2013.01); *A61M 2025/107* (2013.01); *A61M 2025/109* (2013.01)

(58) Field of Classification Search
None
See application file for complete search history.

(56) References Cited

U.S. PATENT DOCUMENTS 2,854,983 A 10/1958 Baskin
5,176,693 A 1/1993 Pannek, Jr.
(Continued)

FOREIGN PATENT DOCUMENTS

DE 10017147 A1 * 10/2001 ............ A61M 25/09
JP H08-502679 A 3/1996
(Continued)

OTHER PUBLICATIONS

European Patent Office, "Extended European search report," European Application No. 18869708.0, Jun. 29, 2021.
(Continued)

*Primary Examiner* — Manuel A Mendez
(74) *Attorney, Agent, or Firm* — DENTONS Durham Jones Pinegar

(57) ABSTRACT

An exoskeleton device is capable of being positioned over an expandable instrument, such as a balloon catheter. The exoskeleton device may include an expandable section that receives an expander of the expandable instrument. Expansion of the expander may cause the expandable section of the exoskeleton device to expand and force the expandable section of the exoskeleton device against a surface to be treated. The expandable section may be capable of scoring the surface against which it is forced.

19 Claims, 11 Drawing Sheets

(56) References Cited

U.S. PATENT DOCUMENTS

| | | | |
|---|---|---|---|
| 5,336,178 | A | 8/1994 | Kaplan et al. |
| 5,441,515 | A | 8/1995 | Khosravi et al. |
| 5,556,408 | A | 9/1996 | Farhat |
| 5,562,620 | A | 10/1996 | Klein et al. |
| 5,702,410 | A | 12/1997 | Klunder et al. |
| 5,797,935 | A | 8/1998 | Barath |
| 5,855,563 | A | 1/1999 | Kaplan et al. |
| 6,280,411 | B1 | 8/2001 | Lennox |
| 7,252,679 | B2 | 8/2007 | Fischell et al. |
| 8,518,101 | B2 * | 8/2013 | Dreher .................. A61F 2/915 623/1.34 |
| 8,911,398 | B2 | 12/2014 | Chouinard |
| 9,079,000 | B2 | 7/2015 | Hanson et al. |
| 9,114,031 | B2 | 8/2015 | Fulton, III |
| 9,277,935 | B2 | 3/2016 | Fulton, III |
| 9,839,764 | B2 | 12/2017 | Chouinard |
| 11,179,549 | B2 | 11/2021 | Fojtik et al. |
| 2003/0050688 | A1 | 3/2003 | Fischell et al. |
| 2005/0055082 | A1 | 3/2005 | Ben Muvhar et al. |
| 2005/0080472 | A1 | 4/2005 | Atkinson et al. |
| 2005/0080478 | A1 | 4/2005 | Barongan |
| 2005/0267596 | A1 | 12/2005 | Chen et al. |
| 2006/0259005 | A1 | 11/2006 | Konstantino et al. |
| 2006/0271093 | A1 | 11/2006 | Holman et al. |
| 2008/0044553 | A1 | 2/2008 | Freeman et al. |
| 2008/0221666 | A1 | 9/2008 | Licata et al. |
| 2010/0094392 | A1 | 4/2010 | Nguyen et al. |
| 2010/0211161 | A1 | 8/2010 | Dreher |
| 2011/0238154 | A1 | 9/2011 | Murphy et al. |
| 2013/0138081 | A1 | 5/2013 | Stankus et al. |
| 2013/0144328 | A1 | 6/2013 | Weber et al. |
| 2013/0204179 | A1 | 8/2013 | Konstantino et al. |
| 2014/0058421 | A1 | 2/2014 | Lupton |
| 2014/0163594 | A1 | 6/2014 | Schur et al. |
| 2015/0127034 | A1 | 5/2015 | Eaton |
| 2015/0157832 | A1 | 6/2015 | Moelgaard-Nielsen et al. |
| 2015/0313732 | A1 | 11/2015 | Fulton, III |
| 2016/0067071 | A1 | 3/2016 | Jose et al. |
| 2016/0135836 | A1 | 5/2016 | Fulton, III |
| 2017/0065796 | A1 * | 3/2017 | Fojtik ................. A61M 25/104 |
| 2019/0126011 | A1 | 5/2019 | Fojtik et al. |

FOREIGN PATENT DOCUMENTS

| | | |
|---|---|---|
| JP | H10137257 A | 5/1998 |
| JP | 2005503881 A | 2/2005 |
| JP | 2006512952 A | 4/2006 |
| JP | 2010537680 A | 12/2010 |
| JP | 2015173913 A | 10/2015 |
| JP | 2018099485 A | 6/2018 |
| WO | 1994009845 A1 | 5/1994 |
| WO | 2009027531 A2 | 3/2009 |

OTHER PUBLICATIONS

European Patent Office, "Extended European Search Report," European Application No. 16845066.6, Mar. 15, 2019.

Japan Patent Office, "Reasons for Rejection," Japanese Application No. 2020-524127, May 25, 2021.

Japan Patent Office, "Reasons for Rejection," Japanese Application No. 2018-531316, Feb. 19, 2019.

USPTO as International Searching Authority, "International Search Report and Written Opinion," International Application No. PCT/US2020/046242, Nov. 9, 2020.

USPTO as International Searching Authority, "International Search Report," International Application No. PCT/US2018/058057, Jan. 18, 2019.

USPTO as International Searching Authority, "Written Opinion," International Application No. PCT/US2018/058057, Jan. 18, 2019.

USPTO as International Searching Authority, "International Search Report and Written Opinion," International Application No. PCT/US2016/050815, Dec. 1, 2016.

Modern Grinding, "Hypotube Definition," http://moderngrinding.com/hypotube-definition.phpm, 2013.

Japan Patent Office, "Notice of Allowance," Japanese Patent Application No. 2020-524127, Aug. 24, 2023.

European Patent Office, "Communication under Rule 71(3) EPC," European Application No. 18869708.0, Aug. 5, 2024.

Japan Patent Office, "Final Office Action," Japanese Application No. 2020-524127, Feb. 13, 2023.

Japan Patent Office, "Office Action," Japanese Application No. 2020-524127, Apr. 21, 2022.

Japan Patent Office, "Office Action," Japanese Application No. 2019-201214, Oct. 19, 2021.

Japan Patent Office, "Office Action," Japanese Application No. 2019-201214, Aug. 18, 2022.

* cited by examiner

EXOSKELETON DEVICE WITH EXPANDABLE SECTION FOR SCORING

CROSS-REFERENCE TO RELATED APPLICATION

This application is a continuation of U.S. patent application Ser. No. 16/540,046, titled EXOSKELETON DEVICE WITH EXPANDABLE SECTION FOR SCORING ("the '046 application"), now U.S. Pat. No. 11,406,801, issued Aug. 9, 2022 which is a continuation-in-part of U.S. patent application Ser. No. 16/174,205, titled EXOSKELETON DEVICE WITH EXPANDABLE SECTION FOR SCORING ("the '205 application"), now U.S. Pat. No. 11,179,549, issued Nov. 23, 2021. Claims for the benefit of priority were made in the '205 application to the Oct. 27, 2017 filing date of U.S. Provisional Patent Application No. 62/578,378, titled ELONGATED EXOSKELETON ELEMENT FOR USE OVER ELONGATED MEDICAL INSTRUMENTS ("the '378 Provisional Application"), and the Jan. 29, 2018 filing date of U.S. Provisional Patent Application No. 62/623,117, titled ELONGATED EXOSKELETON ELEMENT FOR USE OVER ELONGATED MEDICAL INSTRUMENTS ("the '117 Provisional Application"), are hereby made pursuant to 35 U.S.C. § 119(e). The entire disclosures of the '046 application, the '205 application, the '378 Provisional Application, and the '117 Provisional Application are hereby incorporated herein.

TECHNICAL FIELD

This disclosure relates generally to exoskeleton devices for use on the outer surfaces of elongated medical instruments, such as catheters and balloons (e.g., angioplasty balloons, etc.). More specifically, this disclosure relates to exoskeleton devices with expandable sections that may be expanded and then resiliently return to substantially their original shapes. The expandable section may include struts that rotate upon expansion of the expandable section, with the rotated struts enabling the exoskeleton device to score tissue, a plaque, or another target against which the expanded section is forced, which may enable further treatment (e.g., with medicines, etc.) of the tissue, plaque, or other target.

RELATED ART

Percutaneous transluminal angioplasty (PTA), which is commonly referred to as balloon angioplasty or, even more simply, as angioplasty, is a commonly used minimally invasive endovascular procedure for treating vessels (e.g., arteries, veins, etc.) whose pathways have been narrowed or obstructed (i.e., stenosis of the vessels). As a non-limiting example, angioplasty is often used to surgically treat arterial atherosclerosis (i.e., the formation of plaques on the insides of arterial walls)—a common cause of stenosis. Angioplasty typically involves introducing a deflated balloon catheter to the narrowed or obstructed portion of the vessel, which may be visually confirmed by fluoroscopy, and then inflating the balloon to force the obstructed or narrowed portion of the vessel, including the atherosclerosis, outward. A stent may be placed at that site to hold the newly revascularized portion of the vessel open. Atherosclerosis or, more specifically, the atherosclerotic plaque typically remains in place following angioplasty.

Some PTA and percutaneous transluminal coronary angioplasty (PTCA) balloon catheters include scoring blades. Some examples of such scoring balloon catheters include those marketed under the AngioSculpt trademark by the Philips Healthcare division of Koninklijke Philips N.V. As the balloon of such a device is introduced to a treatment site within a blood vessel of a subject and then expanded, the scoring blades engage the inner surface of the blood vessel and score it. Currently available scoring balloon catheters, such as AngioSculpt® scoring balloon catheters, only include three (3) blades, limiting the number of score marks or cuts that may be made by inflating the balloon once—a single pass. Thus, such a device may not provide an improvement in the effectiveness with which a drug is delivered to and treats the scored tissue. Such a device is typically rotated and re-inflated more than once to provide a more effective number of score marks in the tissue. Nevertheless, the depth of each score is limited by the distance the scoring blades protrude beyond the exterior surface of the balloon, with no currently available scoring balloon catheter providing a score depth of more than about 0.25 mm, which may not be aggressive enough to effectively deliver drugs into the scored tissue.

Angioplasty may be accompanied by treatment with medicines, but that treatment is typically limited to drugs that are administered to the subject for a period of time after the angioplasty procedure has been conducted. As an example, medicines that prevent or treat blood clots (e.g., acetylsalicylic acid (aspirin), and an antiplatelet medication (e.g., clipidogrel), etc.), may be prescribed to a patent for a period of time (e.g., three months, six months, one year, etc.) after angioplasty and stent placement.

SUMMARY

An exoskeleton device according to this disclosure is capable of use with an expandable instrument (e.g., a balloon catheter, etc.). More specifically, an expandable section of an exoskeleton device may include a lumen that can receive the expandable instrument, including an expander of the expandable instrument (e.g., a balloon of the balloon catheter, etc.). The expandable section of the exoskeleton device, or at least a portion of the expandable section, may be capable of expanding, for example, upon expansion (e.g., inflation, etc.) of the expander of the expandable instrument over which that portion of the expandable section is positioned.

In some embodiments, when the expandable section of an exoskeleton device expands, it may be capable of being forced against and scoring an adjacent surface (e.g., an inner surface of a vessel, a surface of a plaque on an inner surface of a vessel, etc.). In a specific embodiment, the expandable section may include a plurality of struts, or spines, positioned around a circumference of the expandable section. Since the struts are positioned around the circumference of the expandable section, each strut may be somewhat arcuate, but substantially flat. Each strut may extend along a length of the expandable section. As the expandable section or a portion thereof expands (e.g., under radial tension, such as an internal force applied by an expander, etc.), portions of adjacent struts may be forced apart from one another, and each strut may rotate (e.g., by up to about 90°, etc.), causing an edge or a corner thereof to be somewhat radially disposed. When in a radially disposed orientation, the edge or corner of each strut, or spine, may engage, or contact, and even score a surface against which the strut is forced.

In a specific embodiment, the expandable section may comprise or be defined from at least a portion of a body of the exoskeleton device, such as a tube (e.g., a hypotube, etc.), which may be formed from a substantially rigid material, such as a metal (e.g., stainless steel, nitinol (nickel titanium), etc.) or a polymer (e.g., polyether ether ketone (PEEK), etc.). Struts may be defined by adjacent rows of slits, with the slits of each row being offset from, or staggered relative to, the slits of an adjacent row. Each row of slits may be positioned along a generator of the expandable section (i.e., a line extending from one end of the expandable section to the other end of the expandable section, parallel to an axis of the expandable section). Each slit may overlap, or be staggered relative to, about half of one slit (if the slit is located at or near an end of the expandable section) or two slits (if the slit is located intermediately along a length of the expandable section) of an adjacent row; stated another way, the slits of an expandable section may have a so-called "brickwork" arrangement, or they may be arranged like the bricks in a so-called "running bond pattern." Such an arrangement may enable a portion of a strut to rotate (e.g., by about 45°, by about 90°, etc.) (or cause rotation of that portion of the strut) upon expansion of a portion of the expandable section on which that strut is located or placement of that strut under radial tension. Such an arrangement, along with the material or materials from which the expandable section is formed, may enable an expanded portion of the expandable section to resiliently return to its relaxed state once radial tension (e.g., from an internal force, etc.) on that portion of the expandable section is released (e.g., when pressure from an expander of an expandable instrument within the expandable section is released, etc.). Thus, there may be no need for a separate resilient element on or within the expandable section. With such an arrangement, when the expandable section is an unexpanded state, or in a relaxed state, its outer surface may be smooth or substantially smooth (accounting for discontinuities that occur as material is removed from the tube to form the slit).

The expandable section of the exoskeleton device may also carry a medicament, which may be delivered to the surface that is engaged or scored while that surface is engaged or scored. The medicament may be carried by edges of the struts, or spines, of the exoskeleton device (e.g., coated onto the edges of the struts, etc.). Such a configuration may enable the exoskeleton device to deliver the medicament to a surface upon expanding the expandable section, or a portion thereof, to cause one or more struts, or spines, of the exoskeleton device to score that surface. Alternatively, the medicament may be introduced into a lumen of the exoskeleton device in a manner that enables it to flow onto or through outer surfaces of the struts while the expandable section is in a fully expanded state (e.g., expanded to a limit defined by a vessel or other structure within which the expandable section is disposed, by a balloon or another expandable instrument within the expandable section, and/or by the expandable section itself), in a partially expanded state, or in an unexpanded state, or a relaxed state.

In addition to the expandable section, the exoskeleton device may include a distal section that is capable of introduction into a subject's body (e.g., into a vessel within the body of a subject, etc.). In some embodiments, a collar may be provided around a distal end of the exoskeleton device or around a distal end of the expandable section. The collar may comprise a smooth, even flexible member. Among other functions, the collar may facilitate introduction of the exoskeleton device into the body of a subject and/or prevent expansion of a distal end of the expandable section.

In addition, a body of the exoskeleton device may include a tubular element (e.g., an extension of the expandable section, a catheter, etc.) coextensive with a proximal end of the expandable section. The tubular element may comprise intermediate and proximal portions of the exoskeleton device. The tubular element may include a lumen that can receive an elongated medical instrument, such as an expandable instrument (e.g., a balloon catheter, etc.) and, thus, may enable placement of the exoskeleton device on the elongated medical instrument. A configuration of the tubular element may enable the tubular element and, thus, the exoskeleton device, to engage the elongated medical instrument, optionally securing the tubular element to the elongated medical instrument. The tubular element may comprise an extension of the portion of the body of the exoskeleton device from which the expandable section is formed or defined. Alternatively, the tubular element may comprise a separately manufactured structure that has been aligned with and secured to the portion of the body that forms or defines the expandable section.

In another aspect, a medical system is disclosed. A medical system according to this disclosure includes an exoskeleton device and an expandable instrument, and may also include a guide wire. The exoskeleton device may be capable of placement over the expandable instrument, or of receiving at least a portion of the expandable instrument, including an expander of the expandable instrument. Any embodiment of exoskeleton device according to this disclosure may be included in a medical system with the expandable instrument. The expandable instrument may have any configuration suitable for the procedure to be performed using the medical system. Without limitation, the expandable instrument may comprise a balloon catheter with a configuration suitable for use in the procedure to be performed. If a guide wire is included in the medical system, it may have a size (e.g., an outer diameter (OD)) suitable for use with the selected expandable instrument and exoskeleton device.

In addition to an exoskeleton device, an expandable instrument, and an optional guide wire, a medical system may include apparatuses that facilitate introduction of the guide wire, the expandable instrument, and/or the exoskeleton device into the body of a subject (e.g., a cannula, an introducer, etc.), apparatuses that work in conjunction with the expandable instrument (e.g., a syringe or another apparatus for expanding the expander of the expandable instrument (e.g., inflating a balloon of a balloon catheter, etc.), etc.), imaging apparatuses, medicaments, and the like.

According to another aspect, methods for using an exoskeleton device are disclosed. Various embodiments of such a method include the introduction of an expandable instrument (e.g., a balloon catheter, etc.) into a subject's body. The expandable instrument may be introduced, or advanced, into the subject's body along a guide wire that was previously placed along a desired path within the subject's body. While advancing the expandable instrument into the subject's body, an expander (e.g., a balloon, etc.) of the expandable instrument may be advanced to a location within the subject's body that is to be treated (e.g., to a narrowed or occluded portion of a vessel, to a plaque in a blood vessel, to a clot, to a diseased or an injured location of a blood vessel, etc.). Advancement of the expandable instrument and its expander may be visualized or otherwise monitored in a manner known in the art (e.g., under fluoroscopy, etc.).

An exoskeleton device may be positioned over the expandable instrument. In some embodiments the exoskeleton device may be positioned over the expandable instrument before the expandable instrument is introduced and advanced into the subject's body and, thus, the exoskeleton device may be introduced and advanced into the subject's body simultaneously with introduction and advancement of the expandable instrument into the subject's body. In other embodiments, the exoskeleton device may be introduced, or advanced, into the subject's body along an expandable instrument that was previously placed along the desired path within the subject's body (e.g., by introducing the expandable instrument into a lumen of the exoskeleton device and introducing and advancing the exoskeleton device over the expandable instrument, etc.). Positioning of the exoskeleton device over the expandable instrument may include placement of an expandable section of the exoskeleton device over an expander of the expandable instrument. If necessary, the position of one or both of the expandable section of the exoskeleton device and the expander of the expandable instrument may be modified or adjusted relative to a location that is to be treated within the subject's body. As an example, the expandable section of the exoskeleton device and the expander of the expandable instrument may be moved together relative to a site that is to be treated. As another example, the expander of the expandable instrument may be moved relative to the expandable section of exoskeleton device and, optionally, relative to a treatment site within body of a subject.

With the expandable section of the exoskeleton device and the expander of the expandable instrument at desired locations within a subject's body, the expander of the expandable instrument may be expanded. Expansion of the expander of the expandable instrument may cause the expandable section of the exoskeleton device to expand. Expansion of the expandable section of the exoskeleton device may force members of the expandable section, including edges or corners of the as struts, against the location that is to be treated. As the edges or corners of the struts of the expandable section are forced against the location that is to be treated, the edges or corners of the struts of the expandable section may engage and even score that location.

Other embodiments of use of an exoskeleton device according to this disclosure may include introduction advancement of the exoskeleton device into a subject's body along a guide wire that was previously placed along a desired path within the subject's body. Advancement of the exoskeleton device may include advancement of an expandable section of the exoskeleton device to a treatment site within the subject's body (e.g., to a narrowed or occluded portion of a vessel, to a plaque in a blood vessel, to a clot, to a diseased or an injured location of a blood vessel, etc.). Advancement of the exoskeleton device and its expandable section may be visualized or otherwise monitored in a manner known in the art (e.g., under fluoroscopy, etc.).

With the exoskeleton device in place, the expandable element may expand. Expansion of the expandable element may include introducing an expandable instrument into a lumen of the exoskeleton device and advancing the expandable instrument into the subject's body through the exoskeleton device. Advancement of the expandable instrument may continue until an expander of the expandable instrument reaches a desired location within the expandable section of the exoskeleton device, which may be confirmed visually or in any other suitable manner known in the art (e.g., under fluoroscopy, etc.). If necessary, the position of one or both of the expandable section of the exoskeleton device and the expander of the expandable instrument may be modified or adjusted relative to a location that is to be treated within the subject's body. The expander of the expandable instrument may then be expanded to expand at least a portion of the expandable section of the exoskeleton device.

In embodiments where a relatively short expander of an expandable instrument is moved and used at a plurality of different locations within a relatively long expandable section of an exoskeleton device, the relatively long expandable section may be positioned along a relatively long treatment site. The relatively short expander may be positioned at a first position along the length of the relatively long expandable section. With the relatively short expander at the first position, the relatively short expander may be expanded to cause that portion of the relatively long expandable section to expand, which may cause the edges or corners of struts of the relatively long expandable section to engage or score a first part of the relatively long treatment site. The relatively short expander may then be moved to one or more further locations along the length of the relatively long expandable section and expanded to cause the relatively long expandable section to expand at each further location, which may cause edges of corners of struts at the further location along the length of the expandable section to engage or score (a) corresponding further part(s) of the relatively long treatment site.

The extent to which the expandable element of the exoskeleton device is expanded may be sufficient to cause struts to rotate, but not to plastically deform the expandable element, which may prevent the expandable element from resiliently contracting substantially to its original unexpanded shape and dimensions. Thus, expansion of an expandable element may have a lower limit and an upper limit. Rotation of the struts and non-plastic vs. plastic deformation of the expandable section may be functions of the material from which the expandable element is formed, its dimensions (e.g., outer diameter, wall thickness, inner diameter (ID), etc.), and the extent to which the slits that define the struts are opened as the expandable element expands (e.g., the angles formed at the ends of the slits during expansion of the expandable element, etc.).

In embodiments where the members of the expandable section carry a medicament, the medicament may be transferred to the locations that have been engaged by the edges or corners of struts of the expandable section and introduced into any scores that have been formed at those locations. Thus, use of the exoskeleton device may the direct application of one or more medicaments to a treatment site (e.g., to the cause of a stenosis, such as an atherosclerotic plaque, etc.), and facilitate uptake of the one or more of medicaments by the treatment site.

Once the desired treatment is complete, the expander of the expandable instrument may be contracted (e.g., the balloon of a balloon catheter may be deflated, etc.), enabling the expandable section of the exoskeleton device to transition from an expanded state to an unexpanded state. The expandable section of the exoskeleton device and the expander of the expandable instrument may then be moved (e.g., advanced, withdrawn, etc.) to another treatment site. Alternatively, the exoskeleton device and the expandable instrument may be removed from the subject's body.

Other aspects of the disclosure, as well as features and advantages of various aspects of the disclosed subject matter, will become apparent to those of ordinary skill in the art through consideration of the foregoing disclosure, the accompanying drawings, and the appended claims.

DETAILED DESCRIPTION

Figure 1:
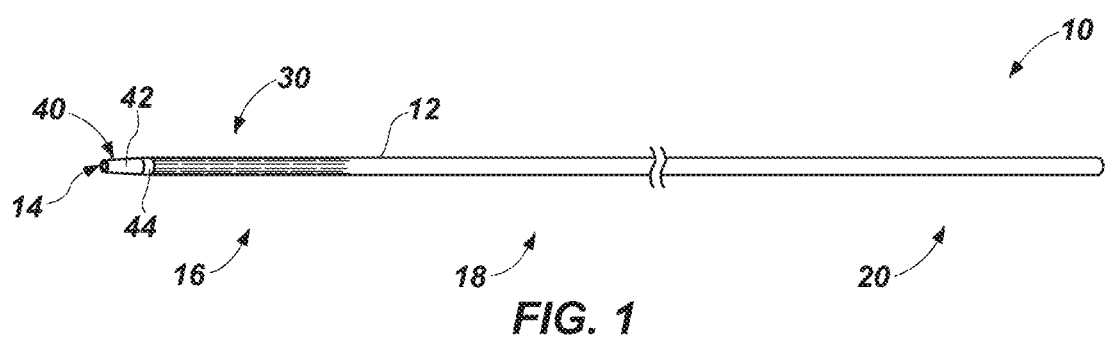
FIG. 1 illustrates an embodiment of an exoskeleton device according to this disclosure, showing an expandable section of the exoskeleton device in an unexpanded state, or a relaxed state.
Figure 2:
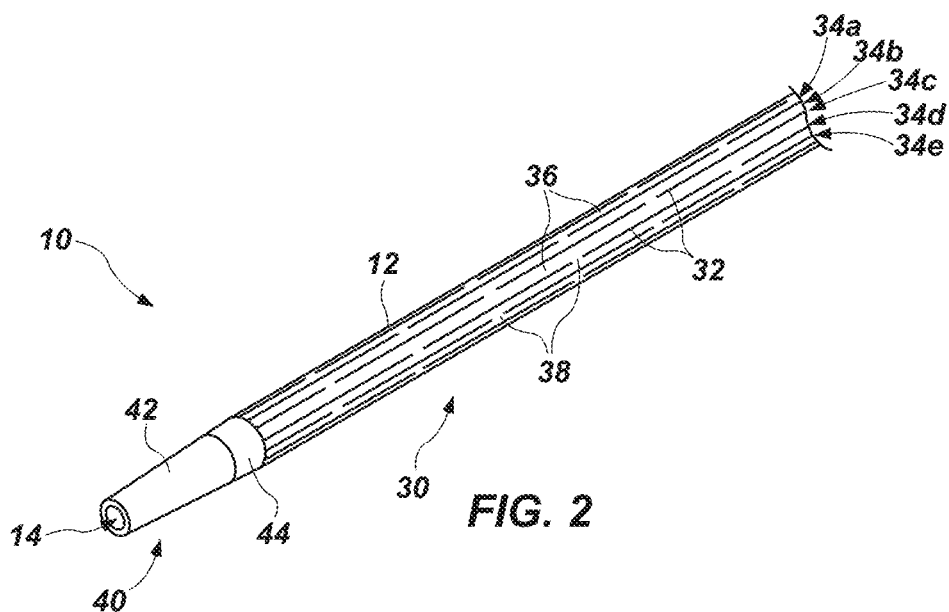
FIG. 2 provides an enlarged orthogonal view of the expandable section of embodiment of exoskeleton device shown in FIG. 1, with the expandable section in the unexpanded state.

An embodiment of an exoskeleton device 10 according to this disclosure is depicted by FIGS. 1-8. The exoskeleton device 10 comprises an elongated medical device with an expandable section 30. The exoskeleton device 10 is at least partially defined by a body 12 that includes a distal portion 16, and intermediate portion 18, and a proximal portion 20.

At least part of the distal portion 16 of the body 12 of the exoskeleton device 10 may have a tubular configuration, through which a lumen 14 is defined. In the depicted embodiment, the body 12 has a tubular configuration along its entire length; thus, the lumen 14 extends through the entire length of the body 12.

The body 12 may comprise a substantially unitary structure or it may include a plurality of assembled elements that have been secured together. In embodiments where the body 12 includes a substantially unitary structure, it may be defined from a single element (e.g., a tube, etc.). An embodiment of the body 12 that includes a plurality of assembled elements may include a distal portion 16 that is formed separately from and subsequently assembled with and joined to a remainder of the body 12, including its intermediate portion 18 and its proximal portion 20.

The body 12 may be formed from any of a variety of suitable materials or from a combination of suitable materials. In some embodiments, the entire body 12 or its distal portion 16 may be defined from or comprise a hypotube, which may be formed from a substantially rigid material, such as a metal. Examples of suitable metals include, but are not limited to stainless steel (e.g., 316L stainless steel, 316 stainless steel, etc.), memory metals (e.g., nitinol, etc.), cobalt chromium (CoCr), nickel chromium (NiCr or nichrome) alloys (including, without limitation, NiCr steel), and the like. Alternatively, the body 12 may be formed from a polymer. A suitable polymer may have a sufficient hardness (e.g., at least 35 Shore D, 35 Shore D to 55 Shore D, 35 Shore D to 72 Shore D, etc.). Examples of suitable polymers include, but are not limited to polyether ether ketone (PEEK), polyimide, nylon, polyether block amides (PEBA, such as that branded as PEBAX®), and extruded plastics (provided that they have a wall 13 thickness that does not exceed the width of their struts 36, as explained below). In embodiments where the body 12 comprises a distal portion 16 that has been formed separately from a remainder of the body 12, the remainder of the body 12 may be formed from any of a variety of suitable materials, including, without limitation, materials from which catheters may be formed (e.g., silicone, nylon, polyurethane, polyethylene, polyethylene terephthalate (PET), polytetrafluoroethylene (PTFE), latex, etc.), as well as a variety of other materials.

The expandable section 30 of the exoskeleton device 10 may be capable of expanding outward (e.g., radially outward, etc.) from an unexpanded state, as shown in FIGS. 1-4, to an expanded state, as depicted by FIGS. 5-8, upon applying an expanding force (e.g., a radially outwardly expanding force, etc.) from within the expandable section 30 to inner surfaces 13$_I$ of the wall 13 of the portion of the body 12 from which the expandable section 30 is defined. The expandable section 30 may be capable of resiliently returning or substantially resiliently returning to the unexpanded state upon removal of the expanding force.

The expandable section 30 of the exoskeleton device 10 may, as illustrated, be located along the distal portion 16 of the body 12 of the exoskeleton device 10. A distal side 32 of the expandable section 30 may be positioned adjacent to a distal end 15 of the body 12. Exoskeleton devices with expandable sections that are located at other positions (e.g. more proximal positions) along the lengths of the bodies of the exoskeleton devices (e.g., along at least part of the intermediate portion 18, along at least part of the distal portion 20, etc.) are also within the scope of this disclosure.

The expandable section 30 may comprise, or be defined by, at least part of the body 12 of the exoskeleton device 10. In the embodiment of exoskeleton device 10 illustrated by FIGS. 1 and 6, the expandable section 30 is defined by series 34a, 34b, 34c, etc., of slits 32 that extend at least partially through a wall 13 of the body 12. In some embodiments, each slit 32 may extend completely through the wall 13 of the body 12, from its outer surface 13$_O$ to its inner surface 13$_I$. In other embodiments, each slit 32 may extend only partially through the wall 13 of the body 12 (e.g., from the outer surface 13$_O$ of the wall 13 toward the inner surface 13$_I$ of the wall 13, etc.). The extent to which each slit 32 extends through the wall 13 of the body 12 may depend, at least in part, upon the material from which the body 12 is formed.

In some embodiments, the cut(s) that define(s) each slit 32 may extend radially through the wall 13 (i.e., toward a longitudinal axis 31 of the expandable section 30). A radially oriented cut may impart the slit 32 with edges that are square or substantially square and that include substantially perpendicular corners.

Figure 4:
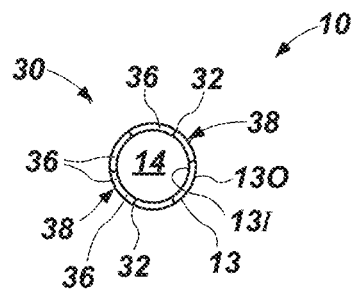
FIG. 4 provides a circumferential cross-sectional view through the expandable section in the unexpanded state, taken along line 4-4 of FIG. 3.
Figure 4A:
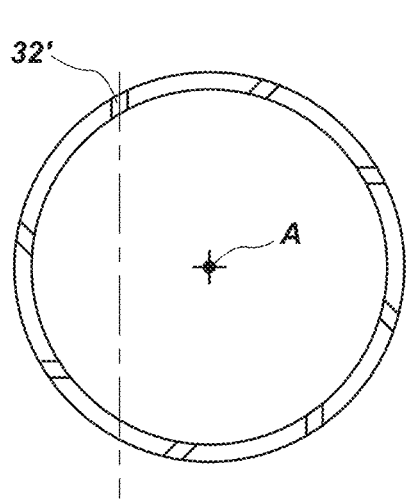
FIGS. 4A and 4B provide circumferential cross-sectional views through other embodiments of expandable sections of exoskeleton devices, with the expandable sections in unexpanded states.
Figure 4B:
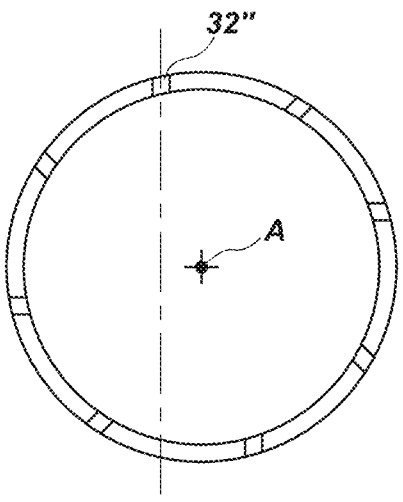

Alternatively, as shown in FIGS. 4A and 4B a slit 32', 32" may be defined by one or more cuts that are oriented non-radially, or off-axis A. Such cuts may define a slit 32', 32" with an edge has an acute corner. Such an edge may resemble a blade or comprise a blade.

With returned reference to FIGS. 1-8, the slits 32 (as well as other embodiments of slits, such as slits 32' and 32" shown in FIGS. 4A and 4B, respectively) and any other embodiment of slit) may be formed by any technique that is compatible with the material from which the body 12 of the exoskeleton device 10 is formed. As a non-limiting example, laser cutting processes may be used to form slits 32 in the body 12.

The slits 32 (with the exception of some slits 32 located at the ends of the expandable section 30) may have the same lengths as one another.

Each series 34a, 34b, 34c, etc., may be defined by linearly aligned slits 32. The slits 32 and each series 34a, 34b, 34c, etc., may extend longitudinally along the body 12, with each series 34a, 34b, 34c, etc., being positioned along a generator of the expandable section 30 (i.e., a line extending from one end of the expandable section 30 to the other end of the expandable section 30, parallel to a longitudinal axis 31 of the expandable section 30). Such an orientation may be referred to as a "straight" orientation.

Adjacent slits 32 in a series 32a, 32b, 32c, etc., are spaced apart by solid, uncut regions of the body 12. These solid regions may be referred to as joints 38 or junctions. The distance across these joints 38, or across the solid regions between adjacent slits 32 in a series 34a, 34b, 34c, etc., may be referred to as the "junction length." The junction length may be tailored to enable expansion of the expandable section 30 and to avoid failure as the expandable section 30 expands. In a specific but nonlimiting embodiment, the junction length between adjacent slits 32 in a series 34a, 34b, 34c, etc., and, thus, across each joint 38 may be 0.014 inch (0.36 mm).

The slits 32 of each series 34b, 34c, 34d, etc., may be offset relative to the slits 32 of each adjacent series 34a, 34b, 34c, 34d, 34e, etc. Each slit 32 in a series 34a, 34b, 34c, etc., may overlap about half of one (if the slit 32 is located at or near an end of the expandable section 30) or two (if the slit 32 is intermediately located along the length of the expandable section 30) circumferentially adjacent slits 32 of each adjacent series 34a, 34b, 34c, etc. Staggering of the slits 32 around the circumference of the distal portion 16 of the body 12 of the exoskeleton device 10 may provide the expandable section 30 with a so-called "brickwork" appearance, with solid portions of the body 12 between the slits 32 arranged in a so-called "running bond pattern." In some embodiments, circumferentially corresponding slits 32 of every other series 34a and 34c, etc., of slits 32 may have equal lengths and be in complete alignment. All of the slits 32 of a circumferentially aligned series 34a, 34b, 34c, etc., of slits 32 may have the same length. In some embodiments, with the exception of smaller slits 32 (e.g., half-length slits 32, etc.) at the ends of an expandable section 30, all of the slits 32 of the expandable section 30 may have the same length. In other embodiments, the length of the slits 32 of one circumferentially aligned series 35a may differ from the length of the slits 32 of another circumferentially aligned series 35b.

Circumferentially adjacent series 34a, 34b, 34c, etc., of slits 32 may be spaced equidistantly around the circumference of the body 12. The expandable section 30 may include an even number of series 34a, 34b, 34c, etc., of slits 32. In embodiments where an even number of circumferentially adjacent series 34a, 34b, 34c, etc., of slits 32 are spaced equidistantly around the circumference of the body 12, each slit 32 of the expandable section 30 may be staggered relative to its circumferentially adjacent slits 32. Alternatively, the distance between slits 32 of one circumferentially adjacent series 34a may differ from the distance between slits 32 of another circumferentially adjacent series 34c; thus, the number of slits 32 of one circumferentially adjacent series 34a may differ from the number of slits 32 of another circumferentially adjacent series 34c.

The solid portions of the body 12 that are located between each adjacent pair of series 34a and 34b, 34b and 34c, 34c and 34d, etc., of slits 32 comprise struts 36 of the expandable section 30. More specifically, each strut 36 may comprise a solid portion of the body 12 between adjacent series 34a and 34b, 34b and 34c, 34c and 34d, etc., of slits 32. Stated another way, each slit 32 comprises a gap between a pair of circumferentially adjacent struts 36.

Staggering of the slits 32 may enable the expandable section 30 to expand, as described in further detail below with reference to FIGS. 5 and 6-8. In some embodiments, as the expandable section 30 expands, the struts 36 may rotate. Such rotation may occur, for example, in embodiments where each ring of circumferentially aligned struts 36 around an expandable section 30 includes an even number of struts 36. As the slits 32 rotate, they protrude outwardly (e.g., radially, etc.) from the circumference of the expandable section 30.

The width of each strut 36 may correspond to the distance the outwardly turned edge of the strut 36 may protrude into a surface (e.g., tissue, etc.) against which it is forced. For example, a strut 36 with a width of about 0.25 mm may be considered to be "less aggressive," a strut 36 with a width of about 0.50 mm may be considered to be "medium" in terms of aggressiveness, and a strut 36 with a width of about 0.75 mm may be considered to be aggressive.

Figure 3:
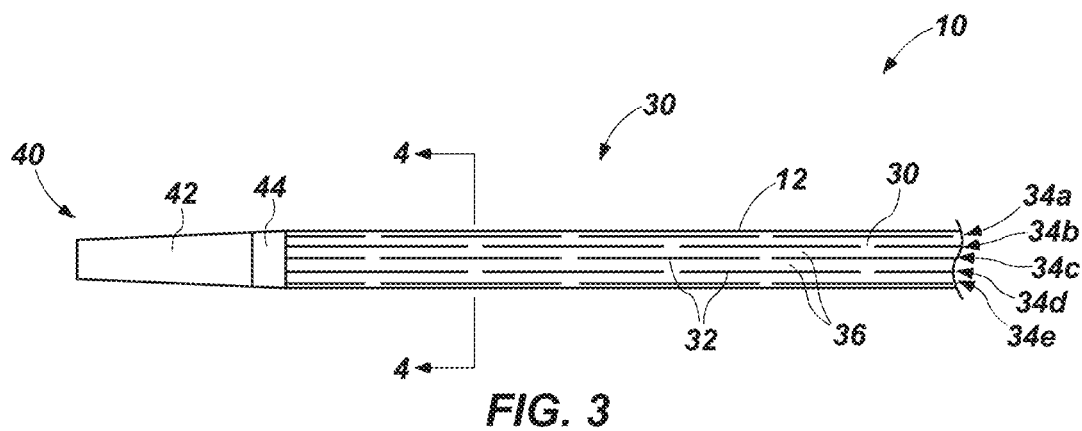
FIG. 3 provides an enlarged side view of the expandable section of the exoskeleton device in the unexpanded state.
Figure 3A:
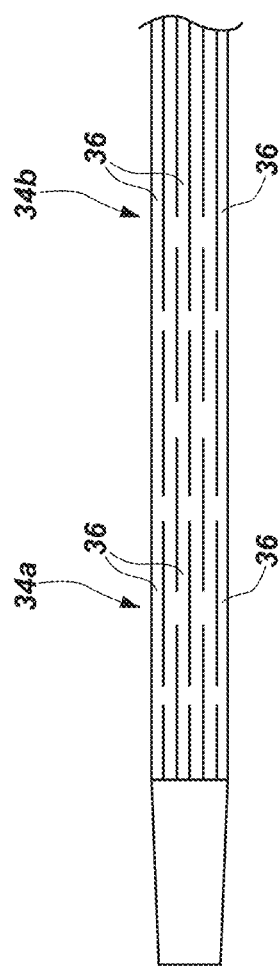
FIG. 3A provides an enlarged side view of another embodiment of expandable section of an exoskeleton device, with the expandable section in an unexpanded state.

As shown in FIG. 3A, the struts 36 of one circumferentially adjacent series 34a may have a width that differs from a width of the struts 36 of another circumferentially adjacent series 34c. Such variable strut width may impart different circumferential portions of an expandable section 30 with flexibilities and/or stiffnesses that differ from one another.

The length of each strut 36 may correspond somewhat to its width. The length of each strut 36 should, however, be short enough to enable the strut 36 to rotate as the expandable section 30 expands. The length of each strut 36 may also be a function of the outer diameter of the body 12 and, thus, the relaxed outer diameter of the expandable section 30. As an example, a strut 36 may have a length of about 4 mm to about 5 mm. Of course, expandable sections 30 with larger outer diameters (e.g., 9F, greater than 9F, etc.) may include longer struts (e.g., about 4 mm long to about 9 mm long).

Figure 3B:
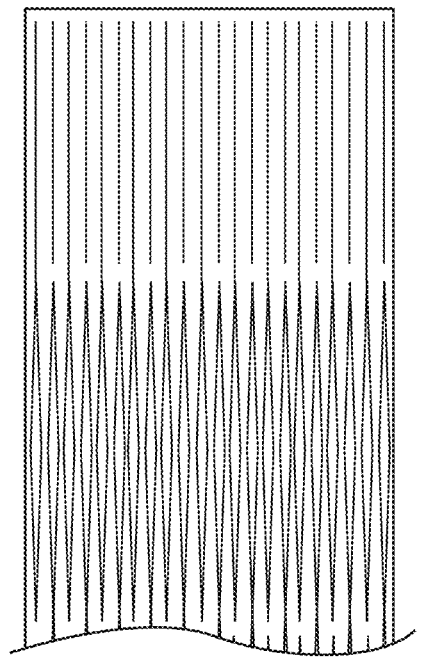
FIG. 3B provides an enlarged side view of yet another embodiment of expandable section of an exoskeleton device, with the expandable section in an unexpanded state.
Figure 3B:
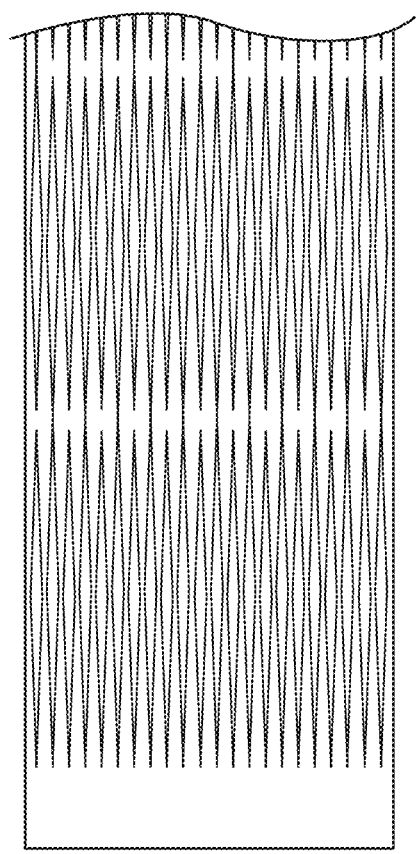

FIGS. 1-8 illustrate an embodiment of expandable section 30 that includes straight slits 32. An expandable section 30' of an exoskeleton device 10' may include slits 32''' with other shapes, such as the smooth diamond, or double diamond shapes depicted by FIG. 3B. Expandable sections 30' that include combinations of differently shaped slits 32, 32''' (e.g., straight slits 32 and double diamond shaped slits 32''', etc.) are also within the scope of this disclosure. As an example, FIG. 3B depicts an embodiment of an expandable section 30''' that includes straight slits 32 at its ends 31P and 31D, and shaped slits 32''' at intermediate locations along the length of the expandable section 30'''.

With reference again returned to FIGS. 1-8, the features that define an expandable section 30 may be tailored. More specifically, the features that define the expandable section 30 may be tailored to impart an expandable section 30 with one or more desired properties. Such tailoring, as well as the resulting properties of the expandable section 30, may be based on the material from which the body 12 of the exoskeleton device 10 is formed, on the dimensions of the body 12 (e.g., the thickness of its wall 13, its inner diameter, its outer diameter, etc.), other factors that may affect the properties of the expandable section 30, or any combination of factors that may affect the properties of the expandable section 30. As an example, the expandable section 30 may include features that impart it with desired amounts of expandability and lateral flexibility, deformability (e.g., struts 36 that rotate to a desired extent upon expansion of the expandable section 30, etc.), and the ability to return to substantially its original shape (i.e., non-plastic deformation and resilience). Without limitation, the number of slits 32 around the circumference of the body 12 (and, thus, the distance between circumferentially adjacent slits 32), the length of each slit 32, and/or the shape of each slit 32 may, individually or in combination, define an expandable section 30 that has desired levels of expandability, lateral flexibility or rigidity, deformability, and resilience.

The extent to which the struts 36 of an expandable section 30 rotate upon expansion of the expandable section 30 depends in part upon the material from which the body 12 of the exoskeleton device 10 is formed and in part upon the extent to which the slits 32 are opened upon expanding the expandable section 30. As an example, a strut 36 may start to rotate when expansion of an expandable section 30 opens the ends of the slits 32 that define the strut 36 by angles of at least about 5° to at least about 15°.

The extent to which the shape of an expandable section 30 is plastically deformed following expansion and release of an expanding force also depends in part upon the material from which the body 12 of the exoskeleton device 10 is formed and in part upon the extent to which the slits 32 are opened upon expanding the expandable section 30. As an example, plastic deformation of the expandable section 30 may not occur until expansion of an expandable section 30 opens the ends of the slits 32 to angles of at least about 25° to at least about 40°.

In embodiments where the body 12 comprises a hypotube formed from 316L stainless steel, the struts 36 will rotate when the expandable section 30 is expanded enough to cause the ends of the slits 32 to open to an angle of at least about 10°. As long as the ends of the slits 32 open to an angle of less than about 30°, the struts 32 may rotate back to their original positions and the expandable section 30 may return to substantially its original shape upon releasing an expanding force from the expandable section 30. Thus, provided expansion of the expandable section 30 only opens the ends of the slits 32 to angles of about 10° to less than about 30°, the struts 36 may rotate outwardly and the expandable section 30 may resiliently return to substantially its original shape. If the expandable section 30 is expanded in a manner that causes the ends of the slits 32 to open by more than about 30°, the expandable section 30 may be plastically deformed, which may prevent the struts 36 from rotating back to their original positions and the expandable section 30 from returning to substantially its original shape.

FIGS. 9-13 provide data for a variety of sizes of exoskeleton devices 10 (FIGS. 1-8). Each of FIGS. 9-13 corresponds to one or more exoskeleton devices 10, each defined from a 316L stainless steel hypotube with a specific embodiment of expandable section 30 that includes double diamond slits 32''' (FIG. 3B), and identifies the extent to which expansion of the expandable section 30 by PTA balloon catheters of a plurality of different sizes, or outer diameters, increases the angles at the ends of the slits 32 (FIGS. 1-8) that define the expandable section 30. FIGS. 9-13 also identify the maximum extent to which each embodiment of expandable section 30 may be expanded while retaining substantially to its original dimensions and shape (i.e., without plastically deforming) in terms of an expansion ratio.

The calculations shown in FIGS. 9-13 identify the angles that an expandable section 30 (FIGS. 1-8) of a certain outer diameter with a certain number of struts 36 (FIGS. 1-8) and struts 36 of a set length will open to when the expandable section 30 is expanded to various specific inner diameters (e.g., with PTA balloon catheters, etc.). Based on these factors, a determination can be made of whether expansion of an expandable section 30 of a particular design and with a particular relaxed outer diameter will, based on the material from which the expandable element 30 is defined (e.g., the material from which the body 12 (FIGS. 1-8) of the exoskeleton device 10 (FIGS. 1-8) of which the expandable element 30 is a part, etc.), will cause the struts 36 to rotate and whether the expandable section 30 will be non-plastically deformed and, thus, whether the expandable section 30 will be able to resiliently return to substantially its original shape and outer diameter or the expandable section 30 will be plastically deformed and, thus, not return to substantially its original shape and outer diameter. In FIGS. 9-13, the angle (α) calculations for each unit of expansion (e.g., 1 mm, 2 mm, 3 mm, 4, mm, 5 mm, 6 mm, 7 mm, etc.) are made by taking the arc tangent of the quotient of the width (w), or arc length, of each strut 36 (FIGS. 1-8) divided by half the length of the strut 36 (½), and then multiplying that value by the product of 180/π and 2 (or 360/π):

$$\alpha = a\tan(w/(\tfrac{1}{2})) *180/\pi *2.$$

Figure 8:
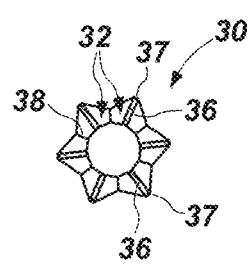
FIG. 8 provides a circumferential cross-sectional view through the expandable section in the expanded state, taken along line 8-8 of FIG. 7.
Figure 9:
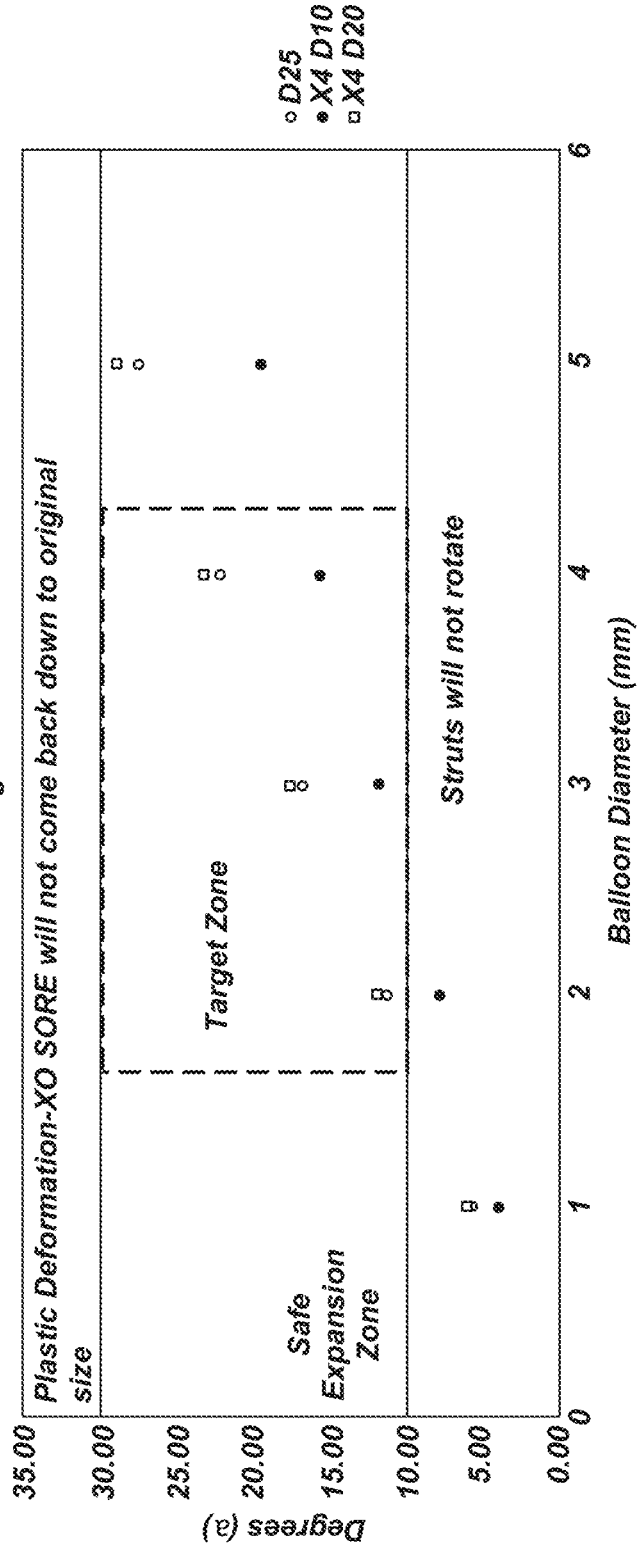
FIGS. 9-13 are charts and corresponding graphs depicting the extents to which the slits of various embodiments of expandable sections of exoskeleton devices are opened upon expanding the expandable sections to different extents and identifying when expansion is sufficient to cause struts of the expandable sections to rotate and to cause the expandable sections to plastically deform.

In FIG. 9, calculations have been made and are illustrated for three different exoskeleton devices 10 (FIGS. 1-8) defined from 4F (1.333 mm OD) hypotubes. A first of the exoskeleton devices D25 includes an expandable section 30 (FIGS. 1-8) with 10 struts 36 (FIGS. 1-8) around each location of the circumference of the expandable section 30. Each strut 36 is defined by a pair of diamond shaped slits 32 (FIGS. 1-8) and has a length of 0.36 inch or 9.144 mm. Longitudinally adjacent slits 32 are spaced 0.014 inch or 0.3556 mm apart from each other.

A second of the exoskeleton devices X4 D10 includes an expandable section 30 (FIGS. 1-8) with 10 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

A third of the exoskeleton devices X4 D20 includes an expandable section 30 (FIGS. 1-8) with 8 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

As the graph of FIG. 9 depicts, the expandable sections 30 (FIGS. 1-8) of exoskeleton devices D25 and X4 D20 must be expanded to inner diameters of about 2 mm (e.g., with a PTA balloon catheter, etc.) or more to cause the struts 36 (FIGS. 1-8) to rotate, while exoskeleton device X4 D10 must be expanded to an inner diameter of about 3 mm (e.g., with a PTA balloon catheter, etc.) or more to cause the struts 36 to rotate. The maximum extent to which the inner diameters of the expandable sections 30 of these devices may be expanded without plastically deforming the expandable sections 30 is slightly more than 4 mm, with the data indicating that the maximum expansion ratio for these embodiments of 4F exoskeleton devices D25, X4 D10, and X4 D20 is 4.239:1.

Figure 10:
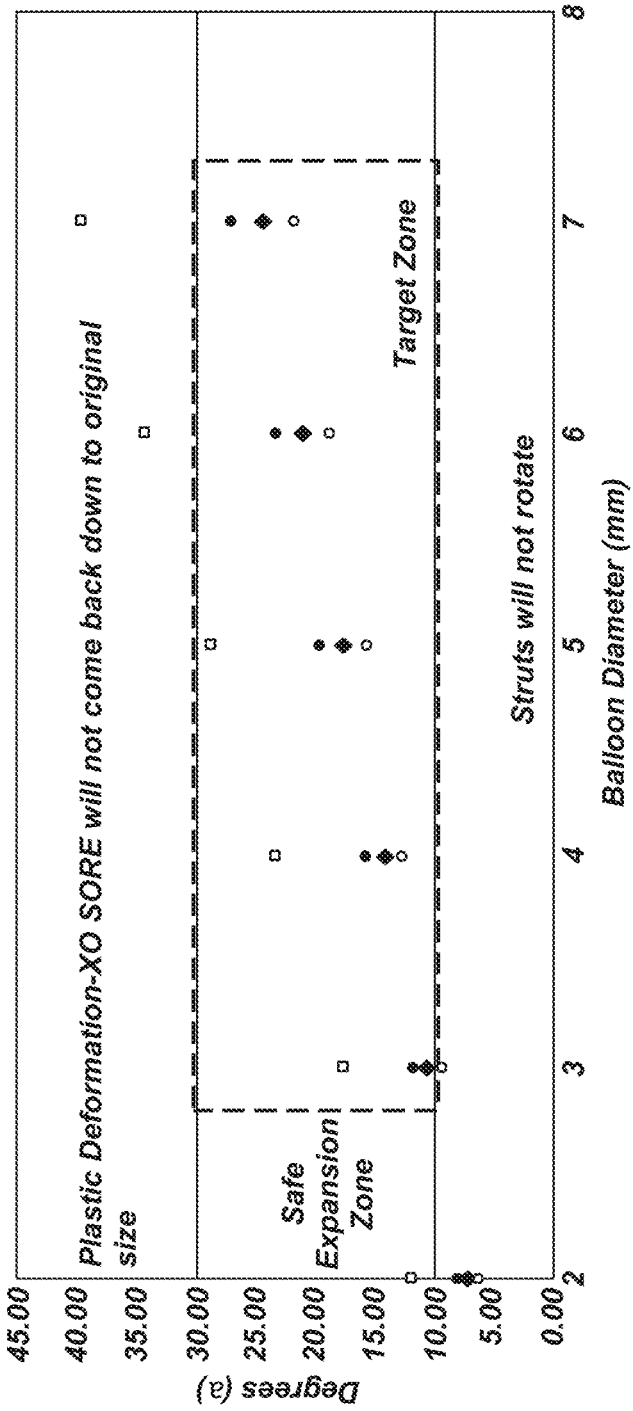

In FIG. 10, calculations have been made and are illustrated for five different exoskeleton devices 10 (FIGS. 1-8) defined from 5F (1.677 mm OD) hypotubes. A first of the exoskeleton devices D25 includes an expandable section 30 (FIGS. 1-8) with 18 struts 36 (FIGS. 1-8) around each location of the circumference of the expandable section 30. Each strut 36 is defined by a pair of diamond shaped slits 32 (FIGS. 1-8) and has a length of 0.5 inch or 12.7 mm. Longitudinally adjacent slits 32 are spaced 0.014 inch or 0.3556 mm apart from each other.

A second of the exoskeleton devices D50 includes an expandable section 30 (FIGS. 1-8) with 10 struts 36 (FIGS. 1-8) around each location of the circumference of the expandable section 30. Each strut 36 is defined by a pair of diamond shaped slits 32 (FIGS. 1-8) and has a length of 0.8 inch or 20.32 mm. Longitudinally adjacent slits 32 are spaced 0.014 inch or 0.3556 mm apart from each other.

A third of the exoskeleton devices X4 D10 includes an expandable section 30 (FIGS. 1-8) with 10 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

A fourth of the exoskeleton devices X4 D20 includes an expandable section 30 (FIGS. 1-8) with 8 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

A fifth of the exoskeleton devices D75 includes an expandable section 30 (FIGS. 1-8) with 8 struts 36 (FIGS. 1-8) around each location of the circumference of the expandable section 30. Each strut 36 is defined by a pair of diamond shaped slits 32 (FIGS. 1-8) and has a length of 1.0 inch or 25.4 mm. Longitudinally adjacent slits 32 are spaced 0.014 inch or 0.3556 mm apart from each other.

As the graph of FIG. 10 depicts, each of the expandable sections 30 (FIGS. 1-8) of exoskeleton devices D25, D50, X4 D10, X4 D20, and D75 must be expanded to inner diameters of about 3 mm (e.g., with a PTA balloon catheter, etc.) or more to cause the struts 36 (FIGS. 1-8) to rotate, while exoskeleton device X4 D10 must be expanded to an inner diameter of about 3 mm (e.g., with a PTA balloon catheter, etc.) or more to cause the struts 36 to rotate. The inner diameter of the expandable section 30 of exoskeleton device X4 D20 may be expanded to about 5 mm without plastically deforming its expandable section 30, while the inner diameters of the expandable sections 30 of exoskeleton devices D25, D50, X4 D10, and D75 may be expanded to about 7 mm or more without plastically deforming their expandable sections 30. The data indicate that the maximum expansion ratio for 5F exoskeleton devices D25, D50, X4 D10, and D75 is 4.239:1.

Figure 11:
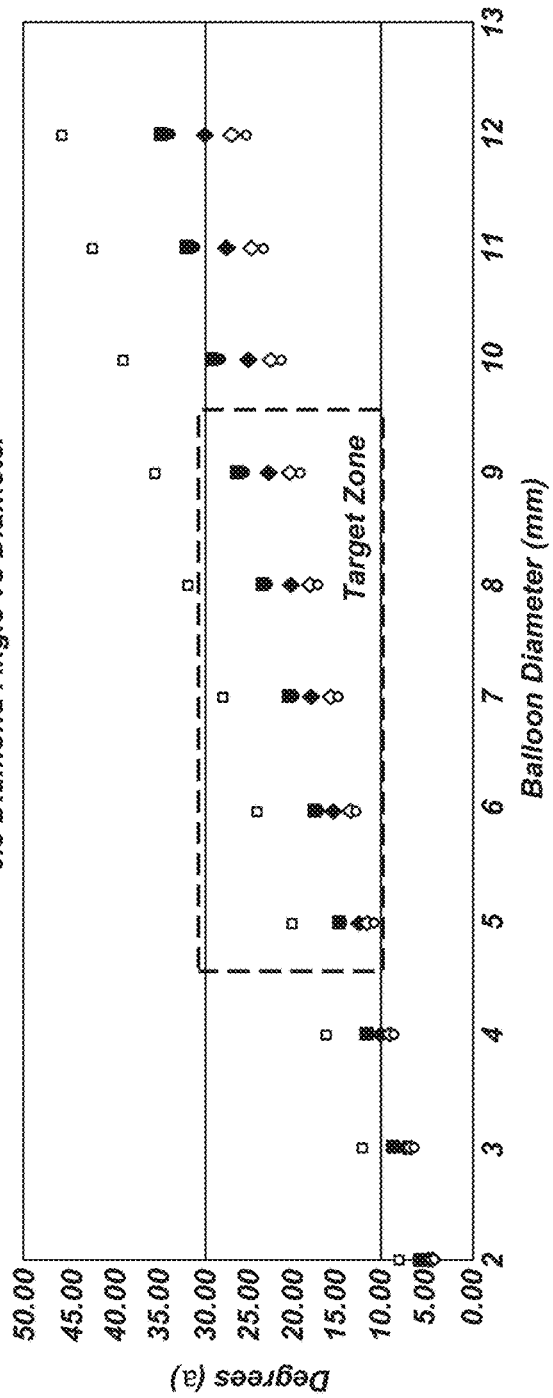

In FIG. 11, calculations have been made and are illustrated for seven different exoskeleton devices 10 (FIGS. 1-8) defined from 6.3F (about 2.1 mm OD) hypotubes. A first of the exoskeleton devices D35.7 includes an expandable section 30 (FIGS. 1-8) with 18 struts 36 (FIGS. 1-8) around each location of the circumference of the expandable section 30. Each strut 36 is defined by a pair of diamond shaped slits 32 (FIGS. 1-8) and has a length of 0.7 inch or 17.78 mm. Longitudinally adjacent slits 32 are spaced 0.014 inch or 0.3556 mm apart from each other.

A second of the exoskeleton devices D25.6 includes an expandable section 30 (FIGS. 1-8) with 22 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

A third of the exoskeleton devices D50.8 includes an expandable section 30 (FIGS. 1-8) with 14 struts 36 (FIGS. 1-8) around each location of the circumference of the expandable section 30. Each strut 36 is defined by a pair of diamond shaped slits 32 (FIGS. 1-8) and has a length of 0.8 inch or 20.32 mm. Longitudinally adjacent slits 32 are spaced 0.014 inch or 0.3556 mm apart from each other.

A fourth of the exoskeleton devices X4 D20 includes an expandable section 30 (FIGS. 1-8) with 10 struts 36 (FIGS. 1-8) around each location of the circumference of the expandable section 30. Each strut 36 is defined by a pair of diamond shaped slits 32 (FIGS. 1-8) and has a length of 0.7 inch or 17.78 mm. Longitudinally adjacent slits 32 are spaced 0.014 inch or 0.3556 mm apart from each other.

A fifth of the exoskeleton devices D50.7 includes an expandable section 30 (FIGS. 1-8) with 14 struts 36 (FIGS. 1-8) around each location of the circumference of the expandable section 30. Each strut 36 is defined by a pair of diamond shaped slits 32 (FIGS. 1-8) and has a length of 0.7 inch or 17.78 mm. Longitudinally adjacent slits 32 are spaced 0.014 inch or 0.3556 mm apart from each other.

A sixth of the exoskeleton devices D50.9 includes an expandable section 30 (FIGS. 1-8) with 14 struts 36 (FIGS. 1-8) around each location of the circumference of the expandable section 30. Each strut 36 is defined by a pair of diamond shaped slits 32 (FIGS. 1-8) and has a length of 0.9 inch or 22.86 mm. Longitudinally adjacent slits 32 are spaced 0.014 inch or 0.3556 mm apart from each other.

A seventh of the exoskeleton devices D50.7 includes an expandable section 30 (FIGS. 1-8) with 16 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

As the graph of FIG. 11 depicts, the struts 36 (FIGS. 1-8) of all of the expandable sections 30 (FIGS. 1-8) of exoskeleton devices D35.7, D25.6, D50.8, X4 D20, D50.7, D50.9, and D10.6 will rotate when the inner diameters of the expandable sections 30 are expanded to about 5 mm, with the struts 36 of the expandable section 30 of exoskeleton device X4 D20 rotating upon expansion of the inner diameter of the expandable section 30 to a diameter to about 2.5 mm or more and the struts 36 of the expandable sections 30 of the exoskeleton devices D50.8, D50.7, and D10.6 rotating upon expansion of the inner diameters of their expandable sections 30 to about 4 mm or more. The inner diameter of the expandable section 30 of exoskeleton device X4 D20 may be expanded to about 7 mm or more without plastically deforming its expandable section 30, while the inner diameters of the expandable sections 30 of exoskeleton devices D35.7, D25.6, D50.8, D50.7, D50.9, and D10.6 may be expanded to about 9 mm or more without plastically deforming their expandable sections 30. The data indicate that the maximum expansion ratio for 6.3F exoskeleton devices D35.7, D25.6, D50.8, X4 D20, D50.7, D50.9, and D10.6 is 3.8:1.

Figure 12:
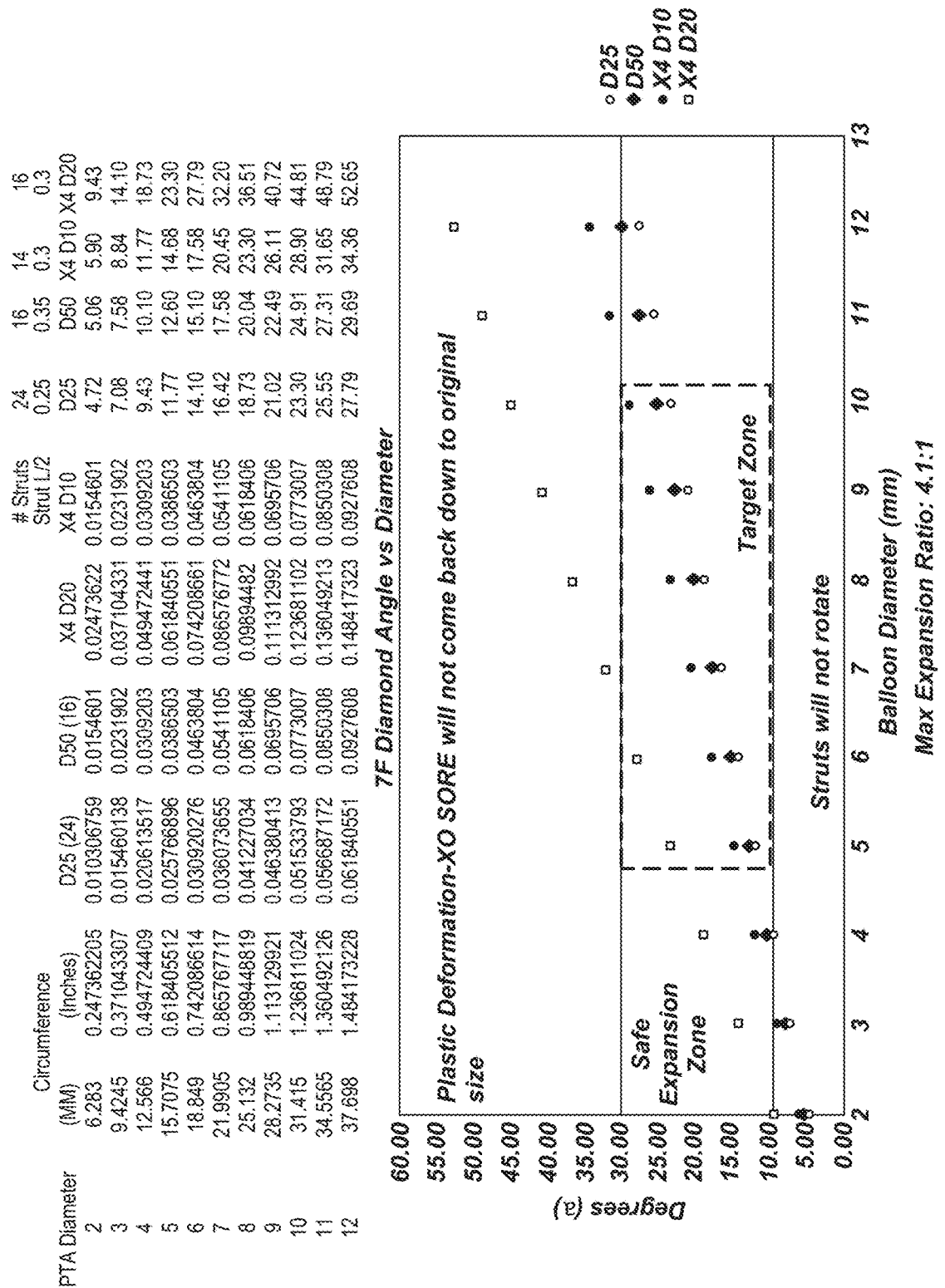

In FIG. 12, calculations have been made and are illustrated for four different exoskeleton devices 10 (FIGS. 1-8) defined from 7F (about 2.333 mm OD) hypotubes. A first of the exoskeleton devices D25 includes an expandable section 30 (FIGS. 1-8) with 24 struts 36 (FIGS. 1-8) around each location of the circumference of the expandable section 30. Each strut 36 is defined by a pair of diamond shaped slits 32 (FIGS. 1-8) and has a length of 0.5 inch or 12.7 mm. Longitudinally adjacent slits 32 are spaced 0.014 inch or 0.3556 mm apart from each other.

A second of the exoskeleton devices D50 includes an expandable section 30 (FIGS. 1-8) with 16 struts 36 (FIGS. 1-8) around each location of the circumference of the expandable section 30. Each strut 36 is defined by a pair of diamond shaped slits 32 (FIGS. 1-8) and has a length of 0.7 inch or 17.78 mm. Longitudinally adjacent slits 32 are spaced 0.014 inch or 0.3556 mm apart from each other.

A third of the exoskeleton devices X4 D10 includes an expandable section 30 (FIGS. 1-8) with 14 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

A fourth of the exoskeleton devices X4 D20 includes an expandable section 30 (FIGS. 1-8) with 16 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

As the graph of FIG. 12 depicts, the struts 36 (FIGS. 1-8) of all of the expandable sections 30 (FIGS. 1-8) of exoskeleton devices D25, D50, X4 D10, and X4 D20 will rotate when the inner diameters of the expandable sections 30 are expanded to about 4 mm or more, with the struts 36 of the expandable section 30 of exoskeleton device D25 rotating upon expansion of the inner diameter of the expandable section 30 to a diameter to about 2 mm or more. The inner diameter of the expandable section 30 of exoskeleton device X4 D20 may be expanded to about 6 mm or more without plastically deforming its expandable section 30, while the inner diameters of the expandable sections 30 of exoskeleton devices D25, D50, and X4 D10 may be expanded to about 10 mm or more without plastically deforming their expandable sections 30. The data indicate that the maximum expansion ratio for 7F exoskeleton devices D25, D50, X4 D10, and X4 D20 is 4.1:1.

Figure 13:
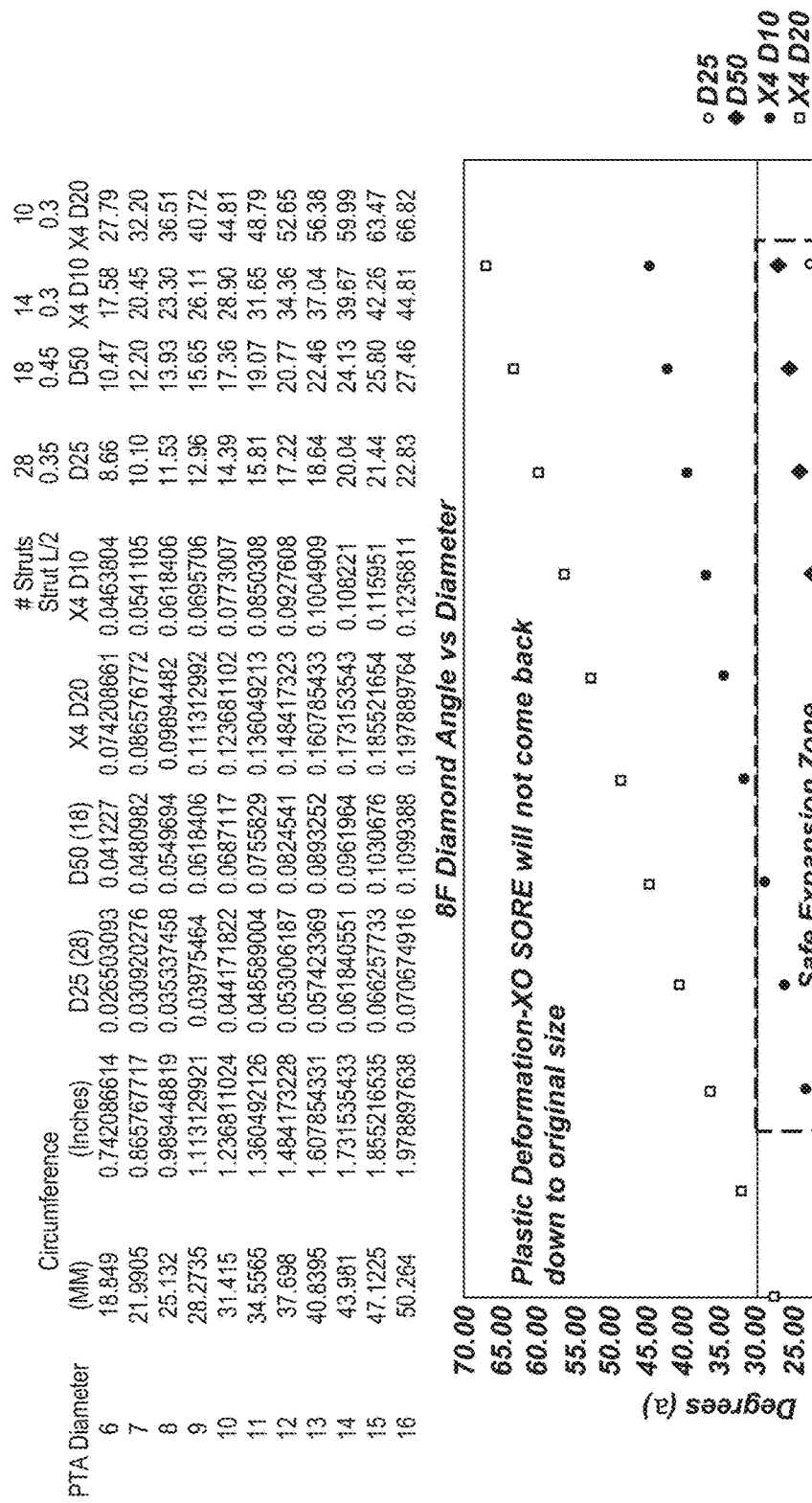
Figure 13:
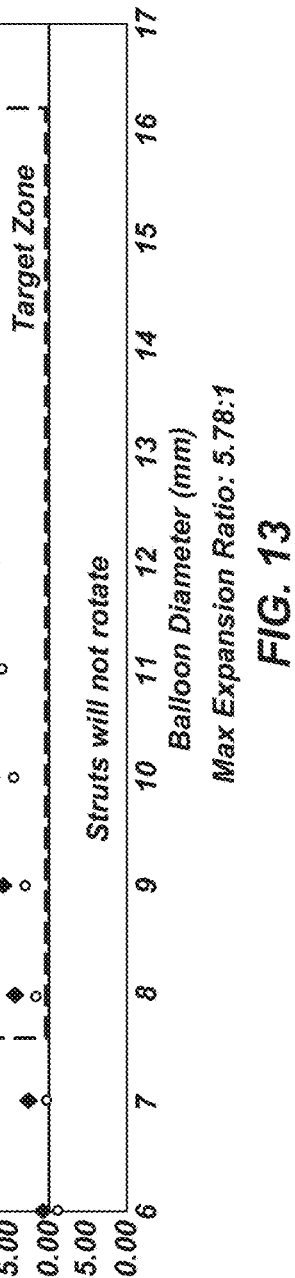

In FIG. 13, calculations have been made and are illustrated for four different exoskeleton devices 10 (FIGS. 1-8) defined from 8F (about 2.667 mm OD) hypotubes. A first of the exoskeleton devices D25 includes an expandable section 30 (FIGS. 1-8) with 28 struts 36 (FIGS. 1-8) around each location of the circumference of the expandable section 30. Each strut 36 is defined by a pair of diamond shaped slits 32 (FIGS. 1-8) and has a length of 0.7 inch or 17.78 mm. Longitudinally adjacent slits 32 are spaced 0.014 inch or 0.3556 mm apart from each other.

A second of the exoskeleton devices D50 includes an expandable section 30 (FIGS. 1-8) with 18 struts 36 (FIGS. 1-8) around each location of the circumference of the expandable section 30. Each strut 36 is defined by a pair of diamond shaped slits 32 (FIGS. 1-8) and has a length of 0.9 inch or 22.86 mm. Longitudinally adjacent slits 32 are spaced 0.014 inch or 0.3556 mm apart from each other.

A third of the exoskeleton devices X4 D10 includes an expandable section 30 (FIGS. 1-8) with 14 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

A fourth of the exoskeleton devices X4 D20 includes an expandable section 30 (FIGS. 1-8) with 10 struts 36 (FIGS. 1-8) around each location of the circumference of the expandable section 30. Each strut 36 is defined by a pair of diamond shaped slits 32 (FIGS. 1-8) and has a length of 0.6 inch or 15.26 mm. Longitudinally adjacent slits 32 are spaced 0.014 inch or 0.3556 mm apart from each other.

As the graph of FIG. 13 depicts, the struts 36 (FIGS. 1-8) of the expandable sections 30 (FIGS. 1-8) of exoskeleton devices D50, X4 D10, and X4 D20 will rotate upon expansion of the inner diameters of the expandable sections 30 to about 6 mm or more, while the struts 36 of the expandable section 30 of exoskeleton device D25 will rotate upon expansion of the inner diameter of the expandable section 30 to a diameter to about 7 mm or more. The inner diameter of the expandable section 30 of exoskeleton device X4 D20 may be expanded up to about 6 mm without plastically deforming its expandable section 30, while the inner diameters of the expandable section 30 of exoskeleton device X4 D10 may be expanded up to about 10 mm without plastically deforming is expandable section 30. And the expandable sections 30 of exoskeleton devices D25 and D50 may be expanded to 16 mm or more without undergoing plastic deformation. The data indicate that the maximum expansion ratio for 8F exoskeleton devices D25, D50, X4 D10, and X4 D20 is 5.78:1.

In a specific embodiment of an exoskeleton device according to this disclosure, the body 12 may comprise a stainless steel (e.g., 316L, 316, etc.) hypotube having an outer diameter of about 0.073 inch (i.e., about 1.85 mm) and an inner diameter of about 0.067 inch (i.e., about 1.7 mm). Thus, the wall 13 of the body 12 may have a thickness of about 0.003 inch (i.e., about 0.076 mm). Twelve (12) series 34a, 34b, 34c, etc., of slits 32 may be arranged equidistantly around the circumference of the body 12, defining twelve (12) struts 36 having widths of about 0.018 inch (i.e., about 0.43 mm), accounting for the width of each slit 32. Each slit 32 may have a length of about one (1) inch (i.e., about 2.54 cm), with adjacent slits 32 in the same series 34a, 34b, 34c, etc., being spaced about 0.015 inch (i.e., about 0.38 mm) apart from each other to define joints 38 having lengths of about 0.015 inch (i.e., about 0.38 mm). Circumferentially adjacent struts 36 may be offset from one another by about half an inch (i.e., about 1.27 cm).

Figure 5:
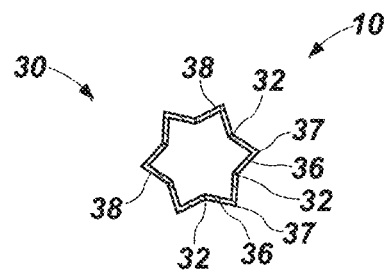
FIG. 5 is a circumferential cross-sectional representation of the expandable section of the exoskeleton device, taken transverse to a longitudinal axis of the exoskeleton device, with the expandable section in a partially expanded state.

As illustrated by FIGS. 1-4, when the expandable section 30 is in its unexpanded state, the outer surface $13_O$ of the wall 13 of the portion of the body 12 from which the expandable section 30 is defined may be substantially smooth, accounting for discontinuities that occur as material is removed from the wall 13 of the body 12 to form each slit 32. As illustrated by FIG. 5, as the expandable section 30 starts to expand, the slits 32 open up and the struts 36 may rotate from circumferentially disposed orientations (i.e., where the outer surface $13_O$ of each strut 36 is oriented along the circumference of the wall 13 of the body 12) to more radial orientations. All of the struts 36 of the expandable section 30 may rotate in the same direction (e.g., counterclockwise, clockwise, etc.). As each strut 36 begins to rotate, an edge 37 of the strut 36 is exposed at an outer extent of the expanded expandable section 30. FIG. 5 shows the expandable section 30 in a partially expanded state, or an intermediate state.

Figure 6:
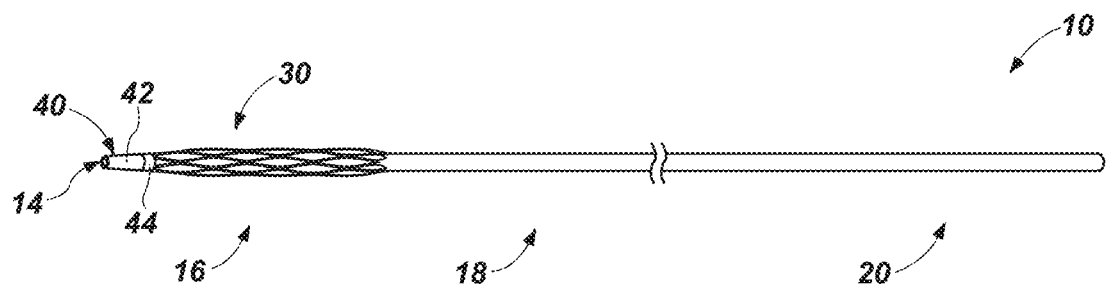
FIG. 6 illustrates the embodiment of the exoskeleton device shown in FIG. 1, showing the expandable section in an expanded state.
Figure 7:
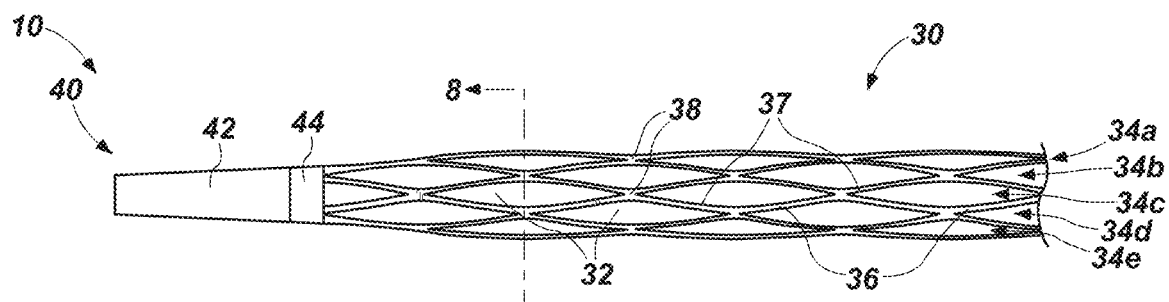
FIG. 7 provides an enlarged side view of the expandable section of the exoskeleton device in the expanded state.

FIGS. 6-8 depict the expandable section 30 of the exoskeleton device 10 in a fully expanded state. As illustrated by FIG. 8, when the expandable section 30 is fully expanded, each strut 36 may rotate by as much as 90°, with each strut 36 being oriented substantially radially.

When the expandable section 30 is in an expanded state (i.e., partially expanded, fully expanded, etc.), the struts 36 and their at least partially outward facing edges 37 may be forced against the location that is to be treated, which may also be referred to herein as a treatment site. As the members of the expandable section are forced against the location that is to be treated, the members of the expandable section may contact that location or even score that location. In embodiments where the members of the expandable section carry a medicament, the medicament may be transferred from the struts 36 to the location that has been treated. The medicament may also be introduced into any scores formed at the location that has been treated.

With returned reference to FIGS. 1 and 6, a distal end 40 of the exoskeleton device 10 may have a configuration that enables its introduction into a subject's body (e.g., into a vessel within the body of a subject, etc.) and its advancement through the subject's body. In some embodiments, the distal end 40 of the exoskeleton device 10 may have a frustoconical configuration (i.e., it may have the shape of a truncated cone, which lacks a pointed tip). Alternatively, the distal end 40 may comprise an open sheath with a slightly tapered outer surface but an inner surface that is not reduced, which may optimize the flow of fluids out of an into the distal end 40. The tapers of distal ends 40 with such configurations may be gradual (e.g., a taper of about 5°, a taper of about 8°, a taper of about 10°, etc.).

A collar 42 may be provided at the distal end 40 of the exoskeleton device 10 and/or at a distal side of the expandable section 30 of the exoskeleton device 10. The collar 42 may facilitate introduction of the exoskeleton device 10 into a subject's body, as well as advancement of the exoskeleton device 10 through the subject's body. Such a collar 42 may be smooth and, optionally, flexible (e.g., it may be formed from a flexible, resilient material, such as silicone, etc.). In some embodiments, the collar 42 may be provided around a distal end of the expandable section 30 to limit expansion at the distal end of the expandable section 30.

A radiopaque marker 44 may be provided at the distal end 40 of the exoskeleton device 10. The distal end 40 may be formed from a radiopaque material (e.g., platinum, etc.) to define the radiopaque marker 44, or a band of radiopaque material may be placed at or near the distal end 40 of the exoskeleton device 10 (e.g., directly adjacent to a distal side of the expandable section 30, etc.). The radiopaque marker 44 may enable visualization (e.g., through fluoroscopy, etc.) of a location of the exoskeleton device 10 and/or its expandable section 30 within a subject's body.

As illustrated by FIGS. 1 and 6, the intermediate portion 18 of the exoskeleton device 10 is located on a proximal side of the expandable section 30, and the proximal portion 20 of the exoskeleton device 10 is located on a proximal side of the intermediate portion 18, closest to an individual (e.g., a healthcare professional, etc.) introducing, advancing, and/or operating the exoskeleton device 10 and any associated devices.

The intermediate portion 18 and/or the proximal portion 20 of the exoskeleton device 10 may be capable of receiving and/or otherwise engaging one or more other elongated medical instruments (e.g., a guide wire, one or more expandable instruments, etc.) (not shown in FIGS. 1-8), including elongated medical instruments that are capable of expanding the expandable section 30 of the exoskeleton device 10 and other medical devices with which the exoskeleton device 10 may be used. In some embodiments, the intermediate portion 18 and, optionally, the proximal portion 20 of the exoskeleton device 10 may comprise a tubular element coextensive with a proximal side of the expandable section 30. The tubular element may include a lumen that can receive the one or more other elongated medical instruments. In some embodiments, the intermediate portion 18 and, optionally, the proximal portion 20 of the exoskeleton device 10 may comprise an extension of the body 12 of the exoskeleton device 10. Alternatively, the proximal portion 20 and, optionally, the intermediate portion 18 of the exoskeleton device 10 may comprise another separately manufactured structure (e.g., a catheter, another tube, a tether, etc.) that may be aligned with and is secured to a proximal end of the body 12 of the exoskeleton device 10.

Figure 14:
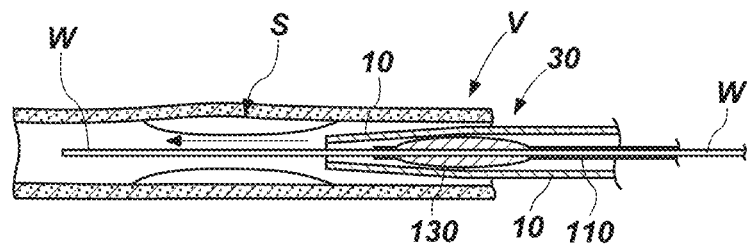
FIG. 14 is a cross-sectional representation showing an embodiment of a technique for introducing an expandable section of an exoskeleton device to a target location within a body of a subject, in which the exoskeleton device and an expandable instrument are pre-assembled with an expandable section of the exoskeleton device positioned over an expander of the expandable instrument, and then the expandable section and the expander are introduced to the target location together in an assembled relationship.
Figure 15:
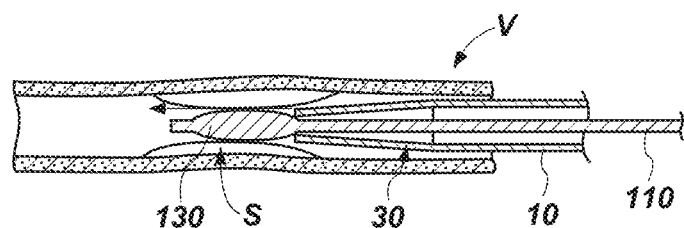
FIG. 15 is a cross-sectional representation showing another embodiment of a technique for introducing an expandable section of an exoskeleton device to a target location within a body of a subject, in which an expander of an expandable instrument is introduced to the target location, and then the exoskeleton device is introduced into the body over the expandable instrument until an expandable section of the exoskeleton device is positioned over the expander of the expandable instrument at the target location.
Figure 16:
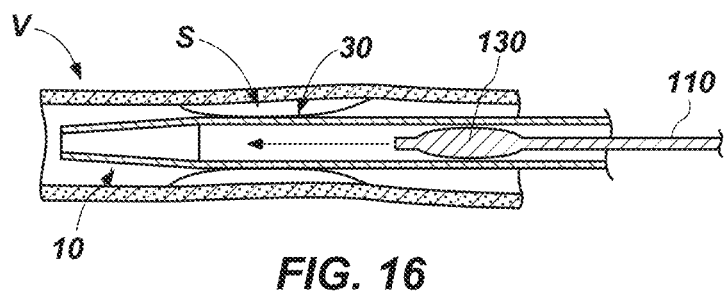
FIG. 16 is a cross-sectional representation showing yet another embodiment of a technique for introducing an expandable section of an exoskeleton device to a target location with a body of a subject, in which the exoskeleton device is introduced into the body of a subject until an expandable section of the exoskeleton device reaches a target location, and then an expandable instrument is introduced into the body through a lumen of the exoskeleton device, until an expander of the expandable instrument is positioned within the expandable section of the exoskeleton device.

Turning now to FIGS. 14-16, embodiments of various techniques for introducing an exoskeleton device 10 (FIGS. 1-8) of this disclosure into a body of a subject are depicted.

In FIG. 14, an embodiment of a technique for introducing an expandable section 30 of an exoskeleton device 10 to a treatment site S, or a target location, within a body of a subject is shown. In that method, a guidewire W is introduced into the subject's body and advanced to and, optionally, through the treatment site S in a manner known in the art. The treatment site S shown in FIG. 14 is a narrowed or occluded location along a vessel V (e.g., a blood vessel, such as an artery or a vein, etc.); it should be noted, however, that the expandable section 30 of the exoskeleton device 10 may be used to treat other organs or features of a subject's anatomy. In FIG. 14, the exoskeleton device 10 and an expandable instrument 110 are pre-assembled, with an expandable section 30 of the exoskeleton device 10 positioned over an expander 130 of the expandable instrument 110. Preassembly of the exoskeleton device 10 and the expandable instrument 110 may include securing the exoskeleton device 10 to the expandable instrument 110. The exoskeleton device 10 and the expandable instrument 110 may then be placed over the guide wire W and introduced into the subject's body together (i.e., simultaneously), and advanced along the guide wire W until the expandable section 30 and the expander 130 reach the treatment site S.

FIG. 15 illustrates another embodiment of a technique for introducing an expandable section 30 of an exoskeleton device 10 to a treatment site S within a subject's body. In the method depicted by FIG. 15, a guidewire W (FIG. 14) is first introduced into the subject's body and advanced through the subject's body to and, optionally, through the treatment site S. With the guidewire W in place, an expandable instrument 110 may then be introduced into the subject's body and advanced through the subject's body until an expander 130 at or near a distal end of the expandable instrument 110 reaches the treatment site S. With the expander 130 at the treatment site S, the guidewire W may, in some embodiments, be removed from the expandable instrument 110 and, thus, from the subject's body. The exoskeleton device 10 may be positioned over the expandable instrument 110 (e.g., a proximal end of the expandable instrument 110 may be placed in a lumen 14 (FIGS. 1 and 4) of the exoskeleton device 10, etc.) and, if the guidewire W remains in place, over the guidewire W. The exoskeleton device 10 may then be introduced into the subject's body and advanced over the expandable instrument 110, through the subject's body until the expandable section 30 is positioned over the expander 130 and at the treatment site S.

FIG. 16 depicts an embodiment of an exoskeleton device 10 introduction and advancement method that includes introducing a guidewire W (FIG. 14) into the subject's body, advancing the guidewire W through the subject's body to the treatment site S, and, optionally, advancing the guidewire W through the treatment site S. With the guidewire W in place, the exoskeleton device 10 may then be introduced into the subject's body and advanced through the subject's body until an expandable section 30 of the exoskeleton device 10 reaches the treatment site S. With the expandable section 30 at the treatment site S, the guidewire W may, in some embodiments, be removed from the exoskeleton device 10 and, thus, from the subject's body. An expandable instrument 110 may be assembled with a proximal portion 20 (FIGS. 1 and 6) of the exoskeleton device 10 (e.g., introduced into a lumen 14 (FIGS. 1 and 4) of the exoskeleton device 10, etc.), and then advanced into the subject's body along the exoskeleton device 10 (e.g., through the lumen 14 of the exoskeleton device 10, etc.), until an expander 130 of the expandable instrument 110 is positioned at a desired location within the expandable section 30 of the exoskeleton device 10 and, thus, at the treatment site S.

Figure 17:
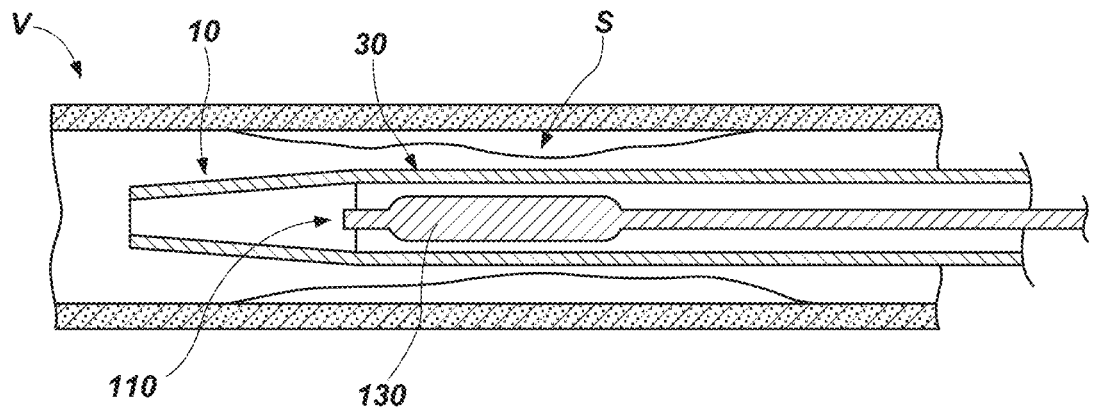
FIG. 17 is a cross-sectional representation showing an embodiment of an expander of an expandable instrument within an embodiment of an expandable section of an exoskeleton device, with the expander and the expandable section in unexpanded, or relaxed, states.
Figure 18:
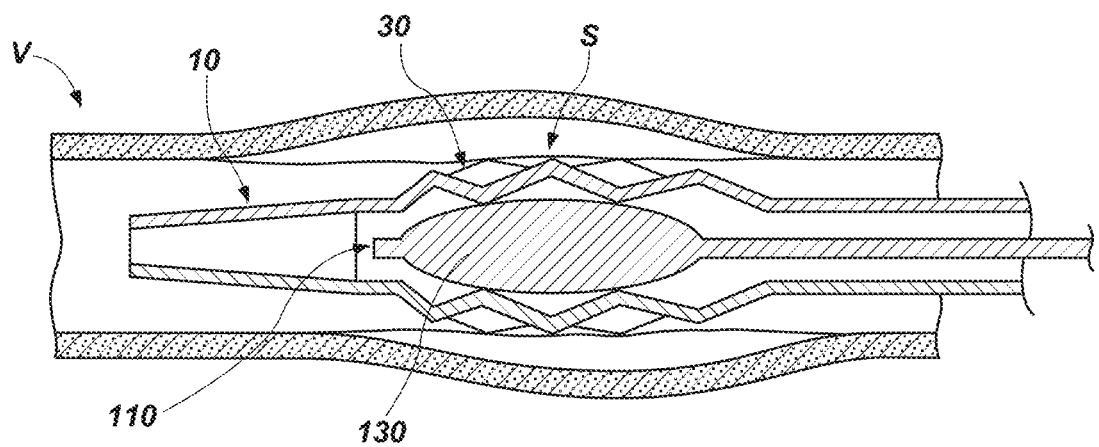
FIG. 18 is a cross sectional representation showing the embodiments of expander and expandable section of FIG. 17 in expanded states.

Regardless of how the expandable section 30 of the exoskeleton device 10 is introduced to the treatment site S and over the expander 130 of the expandable instrument 110, with the expandable section 30 of the exoskeleton device 10 at the treatment site S and the expander 130 of the expandable instrument 110 within the expandable section 30, as shown in FIG. 17, the expander 130 may be expanded in a suitable manner to expand the expandable section 30 (e.g., a balloon of a balloon catheter may be inflated, etc.), as illustrated by FIG. 18. With added reference to FIGS. 5 and 6-8, expansion of the expandable section 30 may cause edges 37 of the struts 36 of the expandable section 30 to contact and, optionally, score locations of the treatment site S (e.g., a diseased site, such as the site of an atherosclerotic plaque or the like; a wounded site; etc.) against which the edges 37 of the struts 36 are forced.

In embodiments such as that depicted by FIG. 16, a plurality of different expandable instruments 110 with differently configured expanders 130 (e.g., balloon catheters with balloons that expand to increasingly larger diameters, etc.) may be sequentially introduced to a treatment site S, operated (or used), and removed from the treatment site S through a single, previously placed exoskeleton device 10. As the expander 130 of an expandable instrument 110 is expanded, it expands the expandable section 30 of the exoskeleton device 10. As the expandable section 30 expands, struts 36 of the expandable section 30 may rotate, outwardly, as shown in FIGS. 5-7. Upon rotating, the struts 36 may engage adjacent tissue (e.g., an interelastic layer (IEL) of a blood vessel (e.g., an artery, a vein, etc.). The extent to which each strut 36 engages the tissue depends upon the width of each strut 36 and the extent to which it rotates as the expandable section 30 expands. In some embodiments, the struts 36 of an expandable section may score or pierce adjacent tissue to a depth of 0.25 mm (e.g., the embodiments of exoskeleton devices labeled "D25" in FIGS. 9, 10, and 12) or more (e.g., 0.50 mm (e.g., the embodiments of exoskeleton devices labeled "D50" in FIGS. 10, and 12), 0.75 mm (e.g., the embodiments of exoskeleton devices labeled "D75" in FIG. 10), etc.). The number of struts 36 around the circumference of the expandable section 30 (e.g., 8, 10, 12, 14, 16, 18, 20, 22, 24, 26, etc.) may define the number of score marks or cuts that can be made in the tissue with a single pass, or expansion, of the expandable section 30. In embodiments where the adjacent tissue comprises the IEL of a blood vessel, such scoring or piercing may safely injure the IEL, enabling more effective drug delivery than that realized by the use of conventional scoring balloon catheters.

Once use of an expander 130 of an expandable instrument 110 is complete, pressure within the expander 130 may be released. The release of pressure within the expander 130 may enable the expandable section 30 to collapse over the expander 130. As the expandable section 30 collapses, the expander 130 may also collapse, or re-wrap, which may facilitate its removal from within the expandable section 30, as well as reintroduction of the expander 130 back into its sheath and, thus, its removal from the exoskeleton device 10 and, thus, from the body of the subject. Thereafter, another medical instrument may be introduced into the body through the exoskeleton device 10. As an example, an expandable instrument 110 with a larger expander 130 may be introduced into the exoskeleton device 10 and used in a manner that expands the expandable section 30 even further (i.e., to a larger radius).

Although the foregoing description provides many specifics, these should not be construed as limiting the scopes of any of the appended claims, but merely as providing information pertinent to some specific embodiments that may fall within the scopes of the appended claims. Features from different embodiments may be employed in combination. In addition, the scopes of the appended claims may encompass other embodiments. All additions to, deletions from, and modifications of the disclosed subject matter that fall within the scopes of the claims are to be embraced by the claims.

What is claimed:

1. An exoskeleton device, comprising:
an expandable section positionable over an expander of an expandable instrument, the expandable section including a plurality of struts, each strut extending along a length of the expandable section, each strut of the plurality of struts including a plurality of sections, each section defined by a pair of parallel slits through the expandable section, an arrangement of slits of the expandable section rendering the expandable section radially expandable and each strut at least partially rotatable upon radial expansion of the expandable section.

2. The exoskeleton device of claim 1, wherein an outer surface of the expandable section is substantially smooth when the expandable section is in an unexpanded state.

3. The exoskeleton device of claim 1, wherein the expandable section includes a plurality of rows of slits, each row of the plurality of rows of slits including a series of slits extending generally along a length of the expandable section.

4. The exoskeleton device of claim 3, wherein the plurality of rows of slits are arranged around the expandable section.

5. The exoskeleton device of claim 3, wherein each slit of the series of slits of each row of the plurality of rows of slits is offset relative to at least one slit of the series of slits of each adjacent row of the plurality of rows of slits.

6. The exoskeleton device of claim 5, wherein each slit that does not extend to an end of the expandable section has a same length as every other slit that does not extend to an end of the expandable section.

7. The exoskeleton device of claim 5, wherein slits of the series of slits of every other row of the plurality of rows of slits have equal lengths and are in complete alignment with one another.

8. The exoskeleton device of claim 5, wherein the arrangement of slits renders the plurality of struts at least partially rotatable under tension.

9. The exoskeleton device of claim 1, wherein the plurality of struts are positioned around the expandable section.

10. An exoskeleton device, comprising:
an expandable section positionable over an expander of an expandable instrument, the expandable section including a plurality of rows of slits arranged around the expandable section, each row of the plurality of rows of slits including a series of slits arranged generally along a length of the expandable section, each slit of the series of slits of each row of the plurality of rows of slits being offset relative to at least one slit of the series of slits of each adjacent row of the plurality of rows of slits, each strut of the plurality of struts being at least partially rotatable.

11. The exoskeleton device of claim 10, wherein each slit that does not extend to an end of the expandable section has a same length as every other slit that does not extend to an end of the expandable section.

12. The exoskeleton device of claim 11, wherein slits of the series of slits of every other row of the plurality of rows of slits have equal lengths and are in complete alignment with one another.

13. The exoskeleton device of claim 10, wherein the expandable section includes a plurality of struts arranged around the expandable section, each strut of the plurality of struts defined between an adjacent pair of rows of slits of the plurality of rows of slits and extending generally along a length of the expandable section.

14. A medical system, comprising:
an exoskeleton device insertable into a body and advanceable through the body along a pathway, the exoskeleton device including an expandable section positionable at a treatment site, the expandable section including a plurality of slits defining a plurality of struts that expand and at least partially rotate upon expansion of the expandable section; and
an expandable instrument with an expander insertable into the expandable section of the exoskeleton device.

15. The medical system of claim 14, wherein the plurality of struts can score a surface against which they are forced upon expansion of the expander of the expandable instrument.

16. The medical system of claim 15, further comprising:
a medicament on the plurality of struts.

17. A method for scoring a surface within a body of a subject, comprising:
positioning an expander of an expandable instrument at least partially within an interior of an expandable section of an exoskeleton device;
introducing the exoskeleton device into the body of the subject, with the expandable section of the exoskeleton device being introduced to a location adjacent to a surface that is to be scored; and
expanding the expander, causing at least a portion of the expandable section of the exoskeleton device to expand with an arrangement of slits in the expandable section enabling portions of struts of the expandable section to move circumferentially apart from one another and to at least partially rotate, forcing at least the portion of the expandable section of the exoskeleton device against the surface that is to be scored, and scoring the surface.

18. The method of claim 17, wherein introducing the exoskeleton device into the body of the subject comprises introducing the exoskeleton device and/or the expandable instrument along a guide wire that has been introduced into the body of the subject.

19. The method of claim 17, further comprising:
introducing a medicament into scores in the surface.

* * * * *